US010707524B2

(12) United States Patent
Yamakaji

(10) Patent No.: US 10,707,524 B2
(45) Date of Patent: Jul. 7, 2020

(54) GRAPHENE COMPOUND AND MANUFACTURING METHOD THEREOF, ELECTROLYTE, AND POWER STORAGE DEVICE

(71) Applicant: SEMICONDUCTOR ENERGY LABORATORY CO., LTD., Atsugi-shi, Kanagawa-ken (JP)

(72) Inventor: Masaki Yamakaji, Kyoto (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 165 days.

(21) Appl. No.: 15/719,620

(22) Filed: Sep. 29, 2017

(65) Prior Publication Data

US 2018/0108944 A1    Apr. 19, 2018

(30) Foreign Application Priority Data

Oct. 19, 2016  (JP) ................. 2016-205177
Oct. 19, 2016  (JP) ................. 2016-205178

(51) Int. Cl.
*H01M 10/0562* (2010.01)
*C07F 7/18* (2006.01)
(Continued)

(52) U.S. Cl.
CPC ....... *H01M 10/0562* (2013.01); *C01B 32/194* (2017.08); *C01B 32/198* (2017.08); *C07D 301/00* (2013.01); *C07D 303/40* (2013.01); *C07F 7/1804* (2013.01); *C07F 7/188* (2013.01); *H01M 10/056* (2013.01); *H01M 10/0525* (2013.01); *B82Y 30/00* (2013.01); *B82Y 40/00* (2013.01); *H01M 2300/0068* (2013.01);
(Continued)

(58) Field of Classification Search
CPC ......... H01M 10/0562; H01M 10/0525; C01B 32/194; C01B 32/198; C07D 301/00; C07D 303/40; C07F 7/1804; C07F 7/188
See application file for complete search history.

(56) References Cited

U.S. PATENT DOCUMENTS 9,505,631 B2    11/2016  Masukuni et al.
2005/0014072 A1   1/2005  Yamaguchi et al.
(Continued)

FOREIGN PATENT DOCUMENTS

JP          2005-038722 A    2/2005

OTHER PUBLICATIONS

Quintana Mildred et al., "Selective organic functionalization of graphene bulk or graphene edges", Jul. 5, 2011, Chem. Commun., 2011, 47, 9330-9332 (Year: 2011).*
(Continued)

*Primary Examiner* — Jimmy Vo
(74) *Attorney, Agent, or Firm* — Nixon Peabody LLP; Jeffrey L. Costellia

(57) ABSTRACT

To provide a graphene compound having an insulating property and an affinity for lithium ions. To increase the molecular weight of a substituent included in a graphene compound. To provide a graphene compound including a chain group containing an ether bond or an ester bond. To provide a graphene compound including a substituent containing one or more branches. To provide a graphene compound including a substituent including at least one of an ester bond and an amide bond.

9 Claims, 10 Drawing Sheets

(51) Int. Cl.
  *H01M 10/056* (2010.01)
  *C01B 32/194* (2017.01)
  *C01B 32/198* (2017.01)
  *C07D 301/00* (2006.01)
  *C07D 303/40* (2006.01)
  *H01M 10/0525* (2010.01)
  *B82Y 30/00* (2011.01)
  *B82Y 40/00* (2011.01)

(52) U.S. Cl.
  CPC .. *H01M 2300/0091* (2013.01); *Y10S 977/734* (2013.01); *Y10S 977/847* (2013.01); *Y10S 977/948* (2013.01)

(56) References Cited

U.S. PATENT DOCUMENTS

| | | | |
|---|---|---|---|
| 2011/0297876 A1 | 12/2011 | Masukuni et al. | |
| 2014/0127568 A1* | 5/2014 | Kawakami | H01M 4/1393 |
| | | | 429/211 |
| 2016/0329533 A1 | 11/2016 | Tajima | |
| 2016/0349905 A1 | 12/2016 | Momma et al. | |
| 2016/0380271 A1 | 12/2016 | Ochiai et al. | |
| 2017/0005364 A1 | 1/2017 | Yamazaki et al. | |
| 2017/0256817 A1 | 9/2017 | Kadoma et al. | |
| 2018/0019462 A1 | 1/2018 | Kadoma et al. | |
| 2018/0076489 A1 | 3/2018 | Mikami et al. | |

OTHER PUBLICATIONS

Sarkar Kishor et al., "Dendron conjugation to graphene oxide using click chemistry for efficient gene delivery", Jun. 1, 2015; RSC Adv., 2015, 5, 50196 (Year: 2015).*

Joshi.T et al., "Effects of Dissolved Transition Metals on the Electrochemical Performance and SEI Growth in Lithium-Ion Batteries", J. Electrochem. Soc. (Journal of the Electrochemical Society), 2014, vol. 161, No. 12, pp. A1915-A1921.

* cited by examiner

FIG. 3A
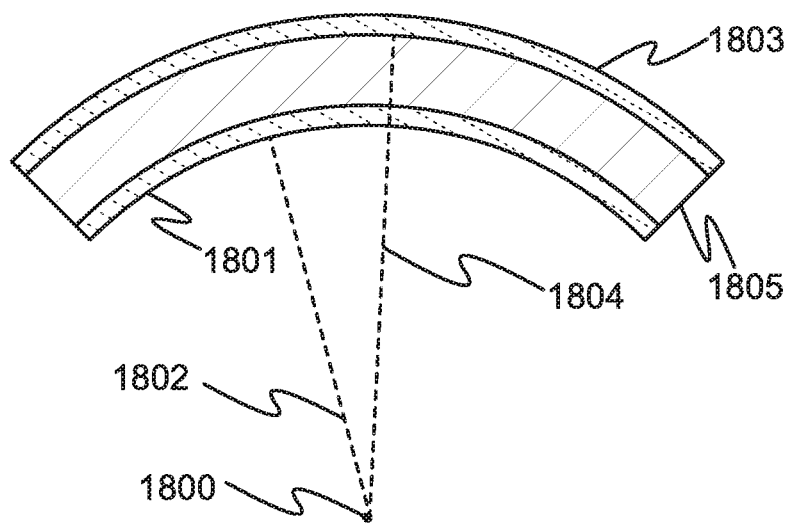
FIG. 3B
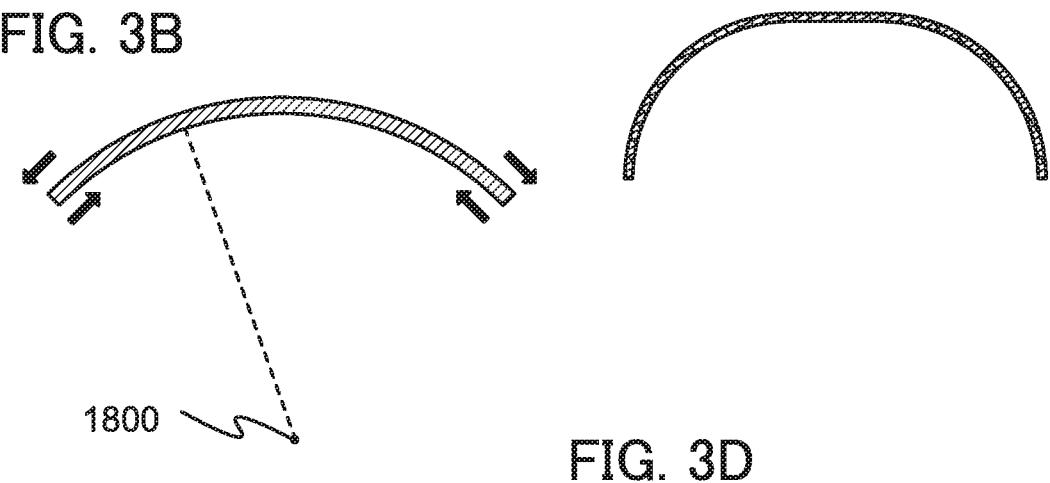
FIG. 3C
FIG. 3D
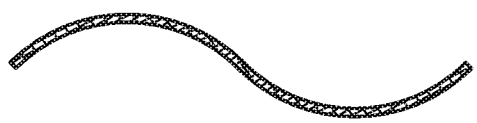

8600

GRAPHENE COMPOUND AND MANUFACTURING METHOD THEREOF, ELECTROLYTE, AND POWER STORAGE DEVICE

BACKGROUND OF THE INVENTION

1. Field of the Invention

One embodiment of the present invention relates to a graphene compound, a manufacturing method of the graphene compound, an electrolyte, and a power storage device.

Note that one embodiment of the present invention is not limited to the above technical field. The technical field of one embodiment of the invention disclosed in this specification and the like relates to an object, a method, or a manufacturing method. Furthermore, one embodiment of the present invention relates to a process, a machine, manufacture, or a composition of matter. Specifically, examples of the technical field of one embodiment of the present invention disclosed in this specification include a semiconductor device, a display device, a light-emitting device, a power storage device, a memory device, a method for driving any of them, and a method for manufacturing any of them.

2. Description of the Related Art

In recent years, a variety of power storage devices, for example, storage batteries such as lithium-ion storage batteries, lithium-ion capacitors, and air cells have been actively developed. In particular, demand for lithium-ion storage batteries with a high output and a high energy density has rapidly grown with the development of the semiconductor industry, for electronic devices, for example, portable information terminals such as mobile phones, smartphones, and laptop computers, portable music players, and digital cameras; medical equipment; next-generation clean energy vehicles such as hybrid electric vehicles (HEVs), electric vehicles (EVs), and plug-in hybrid electric vehicles (PHEVs); and the like. The lithium-ion storage batteries are essential as rechargeable energy supply sources for today's information society.

However, general lithium-ion storage batteries each have high energy density and each include an organic solvent which may catch fire at high temperatures as an electrolyte solution; thus, the lithium-ion storage batteries may generate heat, catch fire, or explode if a protection circuit which controls charge and discharge causes malfunction or a cell is damaged, for example. Such accidents are often reported.

An all-solid-state battery including not an electrolyte solution but a solid electrolyte has been researched as a battery that is less likely to cause such accidents. For example, a power storage device in which a polymer electrolyte having lithium ion conductivity is used as a solid electrolyte has been researched (Patent Document 1).

However, even in a lithium-ion storage battery including a polymer electrolyte, the battery characteristics might be significantly degraded when the temperature of the battery becomes low and the ionic conductivity is significantly decreased. For example, when the battery is used at temperatures lower than the melting point of a polymer contained in the polymer electrolyte, the ionic conductivity of the polymer electrolyte is decreased, which adversely affects the battery characteristics in some cases.

REFERENCE

Patent Document

[Patent Document 1] Japanese Published Patent Application No. 2005-38722

SUMMARY OF THE INVENTION

A solid electrolyte in an all-solid-state battery should have basic properties of high conductivity of ions that transfer electric charges and low conductivity of electrons in order to prevent an internal short circuit between a positive electrode and a negative electrode.

Since a power storage device is used under various environments, a solid electrolyte capable of exhibiting the above-mentioned basic properties even at high temperatures is needed in order to obtain a practical all-solid-state lithium-ion storage battery. That is, a solid electrolyte capable of withstanding high temperatures is needed. For example, a material having excellent heat resistance as well as the properties of a solid electrolyte such as polyethylene oxide (PEO) is needed.

In recent years, deformable electronic devices have been actively developed. In order to obtain such flexible electronic devices, components of the electronic devices also need to be deformable. Not only housings and displays but also power storage devices included in the electronic devices need to be flexible.

In order to obtain a flexible power storage device, components of the power storage device also need to be flexible; thus, a solid electrolyte also needs to be flexible. A ceramic solid electrolyte is widely researched in addition to a polymer-based solid electrolyte such as PEO. Although the ceramic solid electrolyte tends to have higher ionic conductivity than the polymer-based solid electrolyte, the ceramic solid electrolyte is easily broken; thus, it is difficult to use the ceramic solid electrolyte for the flexible power storage device.

In view of the above, an object of one embodiment of the present invention is to provide a material that can be used for a solid electrolyte of a power storage device. Another object is to provide a material having high ion conductivity. Another object is to provide a material having high dispersibility in a solvent. Another object is to provide a material that can withstand high temperatures. Another object is to provide a material that can withstand deformation. Another object is to provide a chemically modified graphene compound. Another object is to provide a novel graphene compound.

Another object of one embodiment of the present invention is to provide a power storage device that can be changed in shape, i.e., a flexible power storage device. Another object is to provide a novel power storage device having flexibility and including a novel graphene compound.

Note that the descriptions of these objects do not disturb the existence of other objects. In one embodiment of the present invention, there is no need to achieve all the objects. Other objects will be apparent from and can be derived from the description of the specification, the drawings, the claims, and the like.

One embodiment of the present invention is a graphene compound including a chain group and a graphene layer. The chain group is bonded to the graphene layer through a first ether bond or a first ester bond. The chain group includes at least one of a second ether bond and a second ester bond.

One embodiment of the present invention is a graphene compound having a structure represented by a general formula (G0).

[Chemical formula 1]

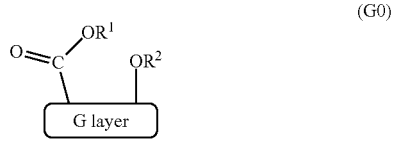

(G0)

In the general formula (G0), G layer represents a graphene layer, one of $R^1$ and $R^2$ represents a chain group including an ether bond or an ester bond, and the other of $R^1$ and $R^2$ represents the chain group or a hydrogen atom.

One embodiment of the present invention is the graphene compound in which, in the general formula (G0) shown above, one of $R^1$ and $R^2$ represents a group represented by a general formula (R-1) and the other of $R^1$ and $R^2$ represents a group represented by the general formula (R-1) or a hydrogen atom.

[Chemical Formula 2]

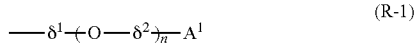

(R-1)

In the general formula (R-1), $\delta^1$ and $\delta^2$ each independently represent a substituted or unsubstituted alkylene group, n represents an integer greater than or equal to 1 and less than or equal to 20, and $A^1$ represents a substituted or unsubstituted alkyl group or hydrogen.

One embodiment of the present invention is the graphene compound in which, in the general formula (G0) shown above, one of $R^1$ and $R^2$ represents a group represented by a general formula (R-2) and the other of $R^1$ and $R^2$ represents a group represented by the general formula (R-2) or a hydrogen atom.

[Chemical Formula 3]

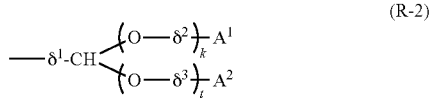

(R-2)

In the general formula (R-2), $\delta^1$ to $\delta^3$ each independently represent a substituted or unsubstituted alkylene group, k represents an integer greater than or equal to 1 and less than or equal to 20, t represents an integer greater than or equal to 1 and less than or equal to 20, and $A^1$ and $A^2$ each independently represent a substituted or unsubstituted alkyl group or hydrogen.

One embodiment of the present invention is the graphene compound in which, in the general formula (G0) shown above, one of $R^1$ and $R^2$ represents a group represented by a general formula (R-3) and the other of $R^1$ and $R^2$ represents a group represented by the general formula (R-3) or a hydrogen atom.

[Chemical Formula 4]

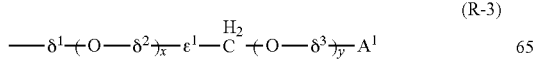

(R-3)

In the general formula (R-3), $\delta^1$ to $\delta^3$ each independently represent a substituted or unsubstituted alkylene group, $\delta^1$ represents an ester bond, x represents an integer greater than or equal to 0 and less than or equal to 20, y represents an integer greater than or equal to 0 and less than or equal to 20, and $A^1$ represents a substituted or unsubstituted alkyl group or hydrogen.

One embodiment of the present invention is the graphene compound in which, in the general formula (G0), one of $R^1$ and $R^2$ represents a group represented by a general formula (R-4) and the other of $R^1$ and $R^2$ represents a group represented by the general formula (R-4) or a hydrogen atom.

[Chemical Formula 5]

(R-4)

In the general formula (R-4), $\delta^1$ to $\delta^3$ each independently represent a substituted or unsubstituted alkylene group, $\delta^1$ represents an ester bond, x represents an integer greater than or equal to 0 and less than or equal to 20, y represents an integer greater than or equal to 0 and less than or equal to 20, and $A^1$ represents a substituted or unsubstituted alkyl group or hydrogen.

One embodiment of the present invention is a graphene compound having a structure represented by a general formula (G1).

[Chemical Formula 6]

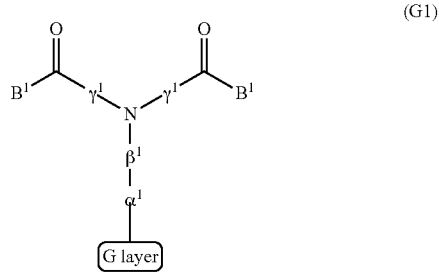

(G1)

In the general formula (G1), G layer represents a graphene layer, $\alpha^1$ represents an ether bond, an ester bond, or a bond represented by a general formula ($\alpha$-1), $\beta^1$ and $\gamma^1$ each independently represent a substituted or unsubstituted alkylene group having 1 to 10 carbon atoms, and $B^1$ represents an alkoxy group or an alkylamino group.

[Chemical Formula 7]

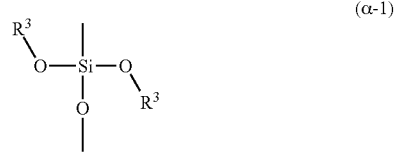

($\alpha$-1)

In the general formula (α-1), $R^3$ represents hydrogen or a substituted or unsubstituted alkyl group having 1 to 10 carbon atoms.

In the graphene compound having the above-described structure, $B^1$ in the general formula (G1) may be a group represented by a general formula (B-1).

[Chemical Formula 8]

(B-1)

In the general formula (B-1), $R^4$ represents a substituted or unsubstituted alkyl group having 1 to 10 carbon atoms.

In the graphene compound having the above-described structure, $B^1$ in the general formula (G1) may be a group represented by a general formula (B-2).

[Chemical Formula 9]

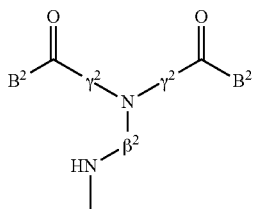

(B-2)

In the general formula (B-2), $\beta^2$ and $\gamma^2$ each independently represent a substituted or unsubstituted alkylene group having 1 to 10 carbon atoms and $B^2$ represents an alkoxy group or an alkylamino group.

In the graphene compound having the above-described structure, $B^2$ in the general formula (B-2) may be a group represented by the general formula (B-1) shown above. In the general formula (B-1), $R^4$ represents a substituted or unsubstituted alkyl group having 1 to 10 carbon atoms.

In the graphene compound having the above-described structure, $B^2$ in the general formula (B-2) may be a group represented by a general formula (B-3).

[Chemical Formula 10]

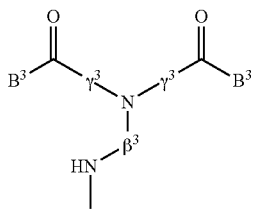

(B-3)

In the general formula (B-3), $\beta^3$ and $\gamma^3$ each independently represent a substituted or unsubstituted alkylene group having 1 to 10 carbon atoms and $B^3$ represents an alkoxy group or an alkylamino group.

In the graphene compound having the above-described structure, $B^3$ in the general formula (B-3) may be a group represented by the general formula (B-1) shown above. In the general formula (B-1), $R^4$ represents a substituted or unsubstituted alkyl group having 1 to 10 carbon atoms.

In the graphene compound having the above-described structure, $B^3$ in the general formula (B-3) may be a group represented by a general formula (B-4).

[Chemical Formula 11]

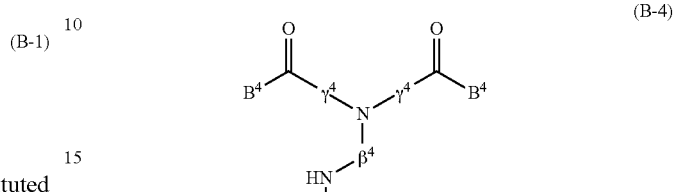

(B-4)

In the general formula (B-4), $\beta^4$ and $\gamma^4$ each independently represent a substituted or unsubstituted alkylene group having 1 to 10 carbon atoms and $B^4$ represents an alkoxy group or an alkylamino group.

In the graphene compound having the above-described structure, $B^4$ in the general formula (B-4) may be a group represented by the general formula (B-1) shown above. In the general formula (B-1), $R^4$ represents a substituted or unsubstituted alkyl group having 1 to 10 carbon atoms.

In the graphene compound having the above-described structure, $B^4$ in the general formula (B-4) may be a group represented by a general formula (B-5).

[Chemical Formula 12]

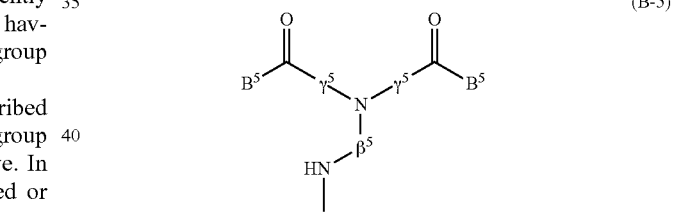

(B-5)

In the general formula (B-5), $\beta^5$ and $\gamma^5$ each independently represent a substituted or unsubstituted alkylene group having 1 to 10 carbon atoms and $B^5$ is represented by the general formula (B-1) shown above. In the general formula (B-1), $R^4$ represents a substituted or unsubstituted alkyl group having 1 to 10 carbon atoms.

One embodiment of the present invention is an electrolyte including the graphene compound having any of the above-described structures and a lithium salt.

One embodiment of the present invention is a power storage device including the graphene compound having any of the above-described structures, an exterior body, a positive electrode current collector, and a negative electrode current collector.

One embodiment of the present invention is a manufacturing method of a graphene compound, including a step of forming a first mixture including graphene oxide and a halide including a chain group containing an ether bond or an ester bond and a step of filtering the first mixture to collect a residue. The residue includes a graphene compound.

In the above-described manufacturing method of a graphene compound, the halide including the chain group containing the ether bond or the ester bond is preferably manufactured by a method including a step of forming a second mixture where alcohol including a chain group containing an ether bond or an ester bond, a reagent, and a solvent are included, and a step of removing the solvent included in the second mixture. The reagent is preferably thionyl chloride, sulfuryl chloride, phosphorus trichloride, phosphorus pentachloride, phosphorus tribromide, phosphorus pentabromide, hydrogen bromide, hydrogen iodide, or cyanuric chloride.

In the above-described manufacturing method of a graphene compound, the halide including the chain group including the ether bond or the ester bond is preferably formed by a method including a step of forming a second mixture where alcohol including a chain group containing an ether bond or an ester bond, triphenylphosphine, and carbon tetrachloride are included, a step of filtering the second mixture to form a third mixture, and a step of removing a solvent included in the third mixture.

One embodiment of the present invention is a manufacturing method of a graphene compound, including a step of forming a first mixture where a graphene compound including a halogen group and alcohol including a chain group containing an ether bond or an ester bond are included, and a step of filtering the first mixture to collect a residue. The residue includes a graphene compound.

In the above-described manufacturing method of a graphene compound, the graphene compound including the halogen group is preferably manufactured by a method including a step of forming a second mixture where graphene oxide, a reagent, and a solvent are included, and a step of removing the solvent included in the second mixture. The reagent is preferably thionyl chloride, sulfuryl chloride, phosphorus trichloride, phosphorus pentachloride, phosphorus tribromide, phosphorus pentabromide, hydrogen bromide, hydrogen iodide, or cyanuric chloride.

One embodiment of the present invention is a manufacturing method of a graphene compound, including a step of forming a mixture including graphene oxide and a compound represented by a general formula (E1) and a step of filtering the mixture to collect a residue. The residue includes a graphene compound.

carbon atoms. In the general formula (B-2), $\beta^2$ and $\gamma^2$ each independently represent a substituted or unsubstituted alkylene group having 1 to 10 carbon atoms and $B^2$ represents an alkoxy group or an alkylamino group.

In the above-described manufacturing method of a graphene compound, $B^2$ in the general formula (B-2) shown above may be a group represented by the general formula (B-1) shown above or a group represented by the general formula (B-3) shown above. In the general formula (B-1) shown above, $R^4$ represents a substituted or unsubstituted alkyl group having 1 to 10 carbon atoms. In the general formula (B-3), $\beta^3$ and $\gamma^3$ each independently represent a substituted or unsubstituted alkylene group having 1 to 10 carbon atoms and $B^3$ represents an alkoxy group or an alkylamino group.

In the above-described manufacturing method of a graphene compound, $B^3$ in the general formula (B-3) shown above may be a group represented by the general formula (B-1) shown above or a group represented by the general formula (B-4) shown above. In the general formula (B-1), $R^4$ represents a substituted or unsubstituted alkyl group having 1 to 10 carbon atoms. In the general formula (B-4), $\beta^4$ and $\gamma^4$ each independently represent a substituted or unsubstituted alkylene group having 1 to 10 carbon atoms and $B^4$ represents an alkoxy group or an alkylamino group.

In the above-described manufacturing method of a graphene compound, $B^4$ in the general formula (B-4) may be a group represented by the general formula (B-1) or a group represented by the general formula (B-5) shown above. In the general formula (B-1), $R^4$ represents a substituted or unsubstituted alkyl group having 1 to 10 carbon atoms. In the general formula (B-5), $\beta^5$ and $\gamma^5$ each independently represent a substituted or unsubstituted alkylene group having 1 to 10 carbon atoms and $B^5$ is represented by the general formula (B-1) shown above. In the general formula (B-1), $R^4$ represents a substituted or unsubstituted alkyl group having 1 to 10 carbon atoms.

One embodiment of the present invention is a manufacturing method of a graphene compound, including a step of forming a mixture including graphene oxide and a compound having a structure represented by a general formula (D1), and a step of filtering the mixture to collect a residue. The residue includes a graphene compound.

[Chemical Formula 13]

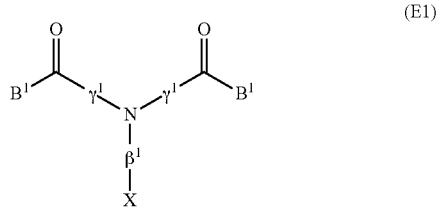

(E1)

In the general formula (E1), $\beta^1$ and $\gamma^1$ each independently represent a substituted or unsubstituted alkylene group having 1 to 10 carbon atoms, $B^1$ represents a substituted or unsubstituted alkyl group having 1 to 10 carbon atoms, and X represents halogen, a trialkoxysilyl group, or a trichlorosilyl group.

In the above-described manufacturing method of a graphene compound, $B^1$ in the general formula (E1) may be a group represented by the general formula (B-1) shown above or a group represented by the general formula (B-2) shown above. In the general formula (B-1), $R^4$ represents a substituted or unsubstituted alkyl group having 1 to 10

[Chemical Formula 14]

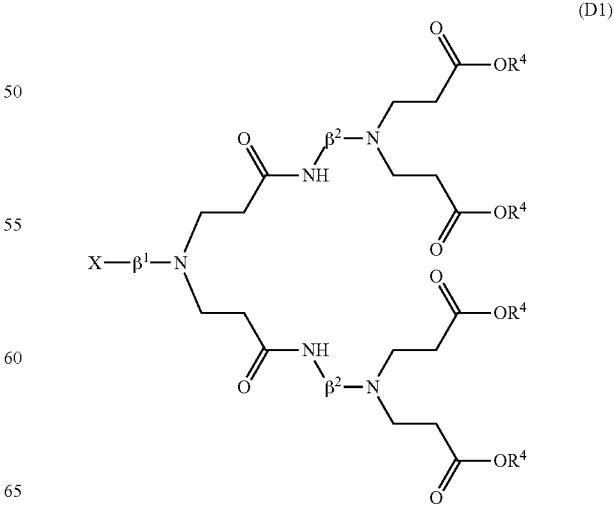

(D1)

In the general formula (D1) shown above, $\beta^1$ and $\beta^2$ each independently represent a substituted or unsubstituted alkylene group having 1 to 10 carbon atoms, $R^4$ represents a substituted or unsubstituted alkyl group having 1 to 10 carbon atoms, and X represents halogen, a trialkoxysilyl group, or a trichlorosilyl group.

One embodiment of the present invention is a manufacturing method of a graphene compound, including a step of forming a first mixture including graphene oxide and a compound having a structure represented by a general formula (D2), and a step of filtering the first mixture to collect a first residue. The first residue includes a graphene compound.

[Chemical Formula 15]

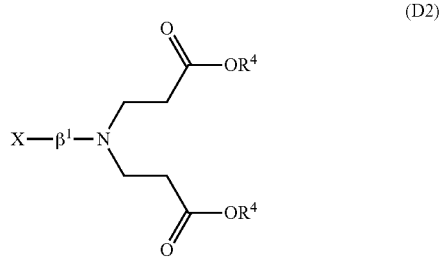

(D2)

In the general formula (D2), $R^4$ represents a substituted or unsubstituted alkyl group having 1 to 10 carbon atoms and X represents halogen, a trialkoxysilyl group, or a trichlorosilyl group.

One embodiment of the present invention is a manufacturing method of a graphene compound, including a step of manufacturing a first graphene compound by any of the above-described manufacturing methods of a graphene compound, a step of forming a second mixture including the first graphene compound and a diamine, and a step of filtering the second mixture to collect a second residue. The second residue includes a second graphene compound.

One embodiment of the present invention is a manufacturing method of a graphene compound, including a step of manufacturing a third graphene compound by any of the above-described manufacturing methods of a graphene compound, a step of forming a third mixture including the third graphene compound and acrylic ester, and a step of filtering the third mixture to collect a third residue. The third residue includes a fourth graphene compound.

According to one embodiment of the present invention, a material that can be used for a solid electrolyte of a power storage device can be provided. A material having high ion conductivity can be provided. A material having high dispersibility in a solvent can be provided. A material that can withstand high temperatures can be provided. A material that can withstand deformation can be provided. A chemically modified graphene compound can be provided. A novel graphene compound can be provided.

According to one embodiment of the present invention, a power storage device that can be changed in shape, i.e., a flexible power storage device can be provided. A novel power storage device having flexibility and including a novel graphene compound can be provided.

Note that the description of these effects does not preclude the existence of other effects. One embodiment of the present invention does not necessarily achieve all the effects listed above. Other effects will be apparent from and can be derived from the description of the specification, the drawings, the claims, and the like.

BRIEF DESCRIPTION OF THE DRAWINGS

FIGS. 3A to 3D illustrate a flexible lithium-ion storage battery.

DETAILED DESCRIPTION OF THE INVENTION

Figure 1A:
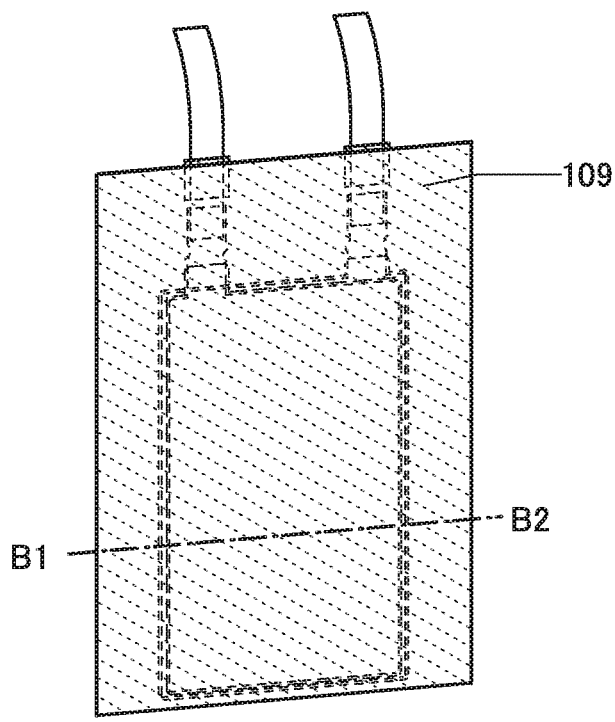
FIGS. 1A and 1B illustrate a lithium-ion storage battery.

Hereinafter, embodiments of the present invention will be described in detail with reference to the accompanying drawings. Note that the present invention is not limited to the description below, and it is easily understood by those skilled in the art that modes and details of the present invention can be modified in various ways. Furthermore, the present invention should not be construed as being limited to the description of the embodiments.

Note that in drawings described in this specification, the sizes, thicknesses, and the like of components such as a positive electrode, a negative electrode, an active material layer, a separator, and an exterior body are exaggerated for simplicity in some cases. Therefore, the sizes of the components are not limited to the sizes in the drawings and relative sizes between the components.

Note that the ordinal numbers such as "first", "second", and "third" in this specification and the like are used for convenience and do not denote the order of steps, the positional relation, or the like. Therefore, for example, description can be made even when "first" is replaced with "second" or "third", as appropriate. In addition, the ordinal numbers in this specification and the like are not necessarily the same as those which specify one embodiment of the present invention.

Note that in the structures of the present invention described in this specification and the like, the same portions or portions having similar functions in different drawings are denoted by the same reference numerals, and descriptions thereof are not repeated. Furthermore, the same hatching pattern is applied to portions having similar functions, and the portions are not especially denoted by reference numerals in some cases.

In this specification, flexibility refers to a property of an object being flexible and bendable. In other words, it is a property of an object that can be deformed in response to an external force applied to the object, and elasticity or restorability to the former shape is not taken into consideration. A flexible object can be deformed in response to an external force. A flexible object can be used with its shape fixed in a state of being deformed, can be used while repeatedly deformed, and can be used in a state of not deformed.

In this specification, chemical modification may refer to changing of a function or a property of a graphene compound by chemically changing the graphene compound. It may refer to addition of a functional group having a certain function or property.

The descriptions in embodiments for the present invention can be combined with each other as appropriate.

Embodiment 1

In this embodiment, a graphene compound formed according to one embodiment of the present invention is described. In addition, a method for forming a graphene compound by chemical modification is described. The graphene compound formed according to one embodiment of the present invention has a function of conducting metal ions such as lithium, sodium, magnesium, and calcium and thus can be used for a solid electrolyte of a lithium-ion storage battery, for example. However, one embodiment of the present invention is not limited thereto.

<Graphene Compound>

First, graphene and a graphene compound are described.

Graphene is a one-atom-thick sheet of carbon atoms having $sp^2$ hybrid orbitals which are bonded to each other and arranged to have a hexagonal lattice structure on a plane. Bonds between carbon atoms in graphene are stronger than those in diamond; thus, graphene has extremely high resistance to deformation and pulling. However, graphene has extremely high electron conductivity and the amount of lithium ions that pass through graphene is insufficient; thus, graphene by itself is not suitable for a solid electrolyte of a lithium-ion storage battery.

Graphene containing carbon atoms arranged in one atomic layer is referred to as single-layer graphene in some cases. Graphene including two or more and one hundred or less layers is referred to as multilayer graphene in some cases. The length in the longitudinal direction or the length of the major axis in a plane in each of single-layer graphene and multilayer graphene is greater than or equal to 50 nm and less than or equal to 100 μm or greater than or equal to 800 nm and less than or equal to 50 μm. Note that graphene in this specification includes single-layer graphene and multilayer graphene.

In general, graphene has various kinds of defects in some cases. For example, a carbon atom forming a lattice may be missing or a five-membered ring or a seven-membered ring may exist in a lattice in addition to a six-membered ring in some cases. In addition, graphene may have a functional group containing carbon or an element other than carbon. Such a defect site can be utilized to bond graphene with an atom or an atomic group to obtain a desired property.

In this specification and the like, a compound including graphene as a basic skeleton is referred to as a graphene compound. Note that in this specification, graphene compounds include single-layer graphene and multilayer graphene.

Graphene compounds are detailed below.

A graphene compound is, for example, a compound where graphene is chemically modified with an atom other than carbon or an atomic group with an atom other than carbon. A graphene compound may be a compound where graphene is chemically modified with an atomic group composed mainly of carbon, such as an alkyl group or an alkylene group. An atomic group that chemically modifies graphene is referred to as a chemically modifying group, a modifying group, a substituent, a functional group, a characteristic group, or the like in some cases. Chemical modification in this specification and the like refers to introduction of an atomic group to graphene, multilayer graphene, a graphene compound, or graphene oxide (described later) by a substitution reaction, an addition reaction, or other reactions.

The chemical modification not only means introduction of one kind of atom or atomic group but also means introduction of two or more kinds of atoms or atomic groups by two or more types of chemical modification. The chemical modification includes an addition reaction of hydrogen, a halogen atom, a hydrocarbon group, an aromatic hydrocarbon group, or a heterocyclic compound group. Examples of a reaction of introducing an atomic group to graphene include an addition reaction and a substitution reaction. Alternatively, a Friedel-Crafts reaction, a Bingel reaction, or the like may be performed. A radical addition reaction may be performed on graphene, and a ring may be formed between graphene and an atomic group by a cycloaddition reaction.

Note that a front surface and a back surface of graphene may be chemically modified with different atoms or different atomic groups. In multilayer graphene, multiple layers may be chemically modified with different atoms or atomic groups.

An example of the above-mentioned graphene compound chemically modified with an atom or an atomic group is graphene chemically modified with oxygen or a functional group containing oxygen. A graphene compound chemically modified with oxygen or a functional group containing oxygen is referred to as graphene oxide in some cases. In this specification, graphene oxides include multilayer graphene oxides.

An example of graphene oxide is represented by a structural formula (300). Although the structural formula (300) shows an example in which a graphene layer (G layer) has an epoxy group, a hydroxy group, and a carboxyl group, the kind and the number of functional groups of the graphene oxide are not limited to those of this example.

[Chemical Formula 16]

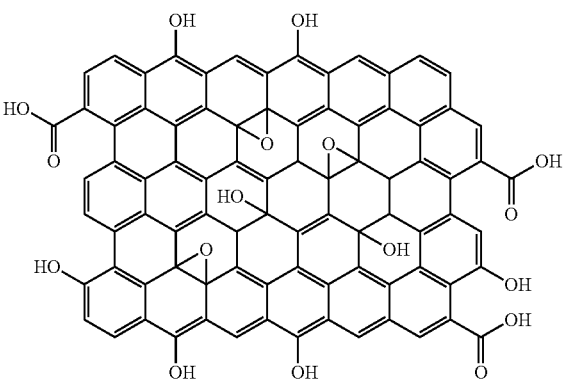

(300)

A simplified structure of graphene oxide is represented by a general formula (G2). A graphene layer is represented by G layer in the general formula (G2). The graphene layer is a sheet-like layer of carbon atoms bonded to each other. The graphene layer may be either a single layer or a multilayer and may include defects or functional groups. Hereinafter, the graphene oxide is described with the general formula (G2). Note that although the graphene layer in the general formula (G2) includes one hydroxy group and one carboxy group, the kind and the number of functional groups of the graphene layer of the present invention are not limited thereto.

[Chemical Formula 17]

(G2)

A formation method example of graphene oxide is described below. Graphene oxide can be obtained by oxidizing the aforementioned graphene or multilayer graphene. Alternatively, graphene oxide can be obtained by being separated from graphite oxide. Graphite oxide can be obtained by oxidizing graphite. The graphene oxide may be further chemically modified with the above-described atom or atomic group.

A compound that can be obtained by reducing graphene oxide is referred to as reduced graphene oxide (RGO) in some cases. In RGO, in some cases, all oxygen atoms contained in the graphene oxide are not extracted and part of them remains in a state of oxygen or an atomic group containing oxygen that is bonded to carbon.

A graphene compound may have a sheet-like shape where a plurality of graphene compounds partly overlap with each other. Such a graphene compound is referred to as a graphene compound sheet in some cases. The graphene compound sheet has, for example, an area with a thickness larger than or equal to 0.33 nm and smaller than or equal to 10 mm, preferably larger than 0.34 nm and smaller than or equal to 10 μm. The graphene compound sheet may be chemically modified with an atom other than carbon, an atomic group containing an atom other than carbon, an atomic group composed mainly of carbon such as an alkyl group, or the like. A plurality of layers in the graphene compound sheet may be chemically modified with different atoms or atomic groups.

A graphene compound may have a five-membered ring composed of carbon atoms or a poly-membered ring that is a seven- or more-membered ring composed of carbon atoms, in addition to a six-membered ring composed of carbon atoms. In the neighborhood of a poly-membered ring that is a seven- or more-membered ring, a region through which a lithium ion can pass may be generated.

A plurality of graphene compounds may be gathered to form a sheet-like shape.

A graphene compound has a planar shape, thereby enabling surface contact.

<Chemically Modified Graphene Compound>

Next, a chemically modified graphene compound is described. A graphene compound formed by a formation method of one embodiment of the present invention can be used for a solid electrolyte of a lithium-ion storage battery, for example. In that case, the graphene compound needs to have an insulating property to prevent a short circuit between a positive electrode and a negative electrode. Note that the graphene compound of one embodiment of the present invention has conductivity to metal ions such as sodium ions, magnesium ions, and calcium ions in addition to lithium ions; thus, the graphene compound of one embodiment of the present invention can be used for applications other than a lithium-ion storage battery. In this embodiment, a power storage device including a lithium ion, which is a typical example of such metal ions, as a carrier is described; the description can also be used for a power storage device including another metal ion as a carrier.

Pure graphene is known to have high electron conductivity, and pure graphene by itself cannot be used for a solid electrolyte of a lithium-ion storage battery. Although graphene oxide has relatively low electron conductivity, it has low reduction resistance and thus is easily reduced to RGO having high electron conductivity. In order to provide graphene oxide or graphene with an insulating property stably, chemical modification is preferably used. For example, graphene oxide or graphene may be chemically modified with a molecule having an alkyl chain that has a relatively large number of carbon atoms. When both surfaces of a sheet-like graphene oxide layer are chemically modified with a compound having a long chain alkyl group, the distance between a plurality of sheets of graphene oxide layers is increased and electronic conduction is suppressed because the alkyl chain contains a functional group having low electron conductivity, so that an insulating property can be provided.

However, an alkyl group is a non-polar functional group and has a low affinity for lithium ions which cause a battery reaction in a lithium-ion storage battery. Thus, when graphene is chemically modified with a compound having a long chain alkyl group, the transfer of lithium ions is inhibited and accordingly a battery reaction is inhibited. Accordingly, a lithium-ion storage battery including a graphene compound chemically modified with a compound having a long chain alkyl group as a solid electrolyte has poor output characteristics.

In view of the above, the graphene compound of one embodiment of the present invention has both an insulating property and an affinity for lithium ions. For example, it is preferable that the graphene compound be chemically modified to have a chain group having an ether bond or an ester bond. The ether bond and the ester bond are classified into a polar group. The ether bond and the ester bond each have an affinity for lithium ions owing to its polarity and contribute to the dissociation of a lithium salt and the transfer of lithium ions. Furthermore, when the graphene compound is used for a solid electrolyte of a lithium-ion storage battery, the number of ether bonds or ester bonds in a functional group of the graphene compound is preferably large because the mobility of lithium ions is improved.

A solid electrolyte including the graphene compound of one embodiment of the present invention has higher heat resistance than a polymer electrolyte using PEO whose melting point is 60° C., for example. High durability is especially important for a lithium-ion storage battery to prevent a serious accident such as firing or explosion caused by an unexpected reaction due to damage to a component in the battery. When a lithium-ion storage battery is used in a severe environment, e.g., in a car, low heat resistance of its component will be a serious problem. The graphene compound of one embodiment of the present invention is similar in structure to graphite, which does not have a melting point, and is unlikely to change in state even at high temperatures. Thus, the graphene compound of one embodiment of the present invention is suitably used as a solid electrolyte of a lithium-ion storage battery that is used at high temperatures.

A general formula (G0) for describing a chemically modified graphene compound of one embodiment of the present invention is shown below.

[Chemical formula 18]

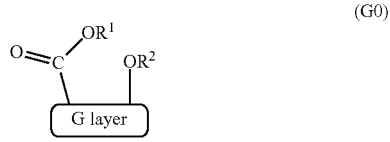

(G0)

In the general formula (G0), G layer represents a graphene layer.

In the general formula (G0), at least one of $R^1$ and $R^2$ is a chain group containing an ether bond or an ester bond. In the general formula (G0), at least one of $R^1$ and $R^2$ may be a hydrogen atom.

In the graphene compound shown in the general formula (G0), the graphene layer is bonded to one chain group mentioned above through an ester bond or bonded to one chain group mentioned above through an ether bond. However, the kind and the number of functional groups bonded to the graphene layer of the present invention are not limited thereto.

Preferably, at least one of $R^1$ and $R^2$ is a chain group containing an ether bond or an ester bond. Interlayer distance in a chemically modified graphene compound may be larger than that in graphene or graphene oxide. As the interlayer distance increases, the electron conductivity becomes low; therefore, the chemically modified graphene compound is favorably used as a solid electrolyte to prevent a short circuit (an internal short circuit) between a positive electrode and a negative electrode. Alternatively, $R^1$ and $R^2$ may be selected as appropriate so that the interlayer distance with which desired electron conductivity is obtained is set.

As the number of ester bonds in $R^1$ or $R^2$ increases, hydrolysis is likely to occur in some cases. As the number of ester bonds in $R^1$ or $R^2$ increases, the molecular weight of $R^1$ or $R^2$ becomes large; thus, reactivity of graphene or graphene oxide at chemical modification is reduced in some cases. Therefore, in the case where at least one of $R^1$ and $R^2$ has one or more ester bonds, the number of ester bonds is preferably 1 to 10.

A chain group containing an ether bond or an ester bond that is at least one of $R^1$ and $R^2$ preferably has a structure represented by the following general formulae (R-1) to (R-4). Note that the chain group containing an ether bond or an ester bond is not limited to the examples shown in the general formulae (R-1) to (R-4).

[Chemical formula 19]

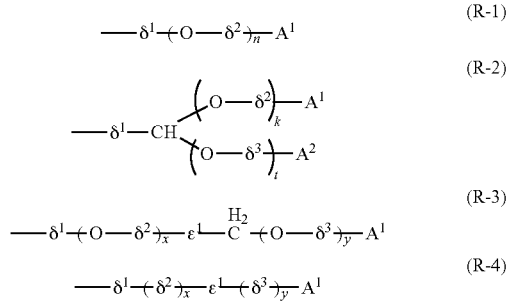

In the general formulae (R-1) to (R-4), $\delta^1$, $\delta^2$, and $\delta^3$ each independently represent a substituted or unsubstituted alkylene group having 1 to 10 carbon atoms.

In the general formula (R-1), n represents an integer greater than or equal to 1 and less than or equal to 20. As n gets larger, the cost of the synthesis increases and the efficiency of a reaction for forming the chemically modified graphene compound decreases. Thus, n is preferably greater than or equal to 1 and less than or equal to 10.

In the general formula (R-2), k and t each independently represent an integer greater than or equal to 0 and less than or equal to 20. It is preferable that k and t be each greater than or equal to 1 and less than or equal to 10.

In each of the general formulae (R-3) and (R-4), $\varepsilon^1$ represents an ester bond.

In each of the general formulae (R-3) and (R-4), x and y each independently represent an integer greater than or equal to 0 and less than or equal to 20. The sum of x and y is preferably greater than or equal to 0 and less than or equal to 10.

In each of the general formulae (R-1) to (R-4), $A^1$ specifically represents hydrogen or a substituted or unsubstituted alkyl group having 1 to 10 carbon atoms.

In the general formula (R-2), $A^2$ specifically represents hydrogen or a substituted or unsubstituted alkyl group having 1 to 10 carbon atoms.

<Chemical Modification>

Next, a method for forming a chemically modified graphene compound by chemically modifying graphene or graphene oxide is described using the following synthesis schemes (S-1) and (S-2). Note that described here is the method for forming a graphene compound in which $R^1$ and $R^2$ in the general formula (G0) are each a chain group containing an ether bond or an ester bond.

[Chemical formula 20]

(S-1)

[Chemical formula 21]

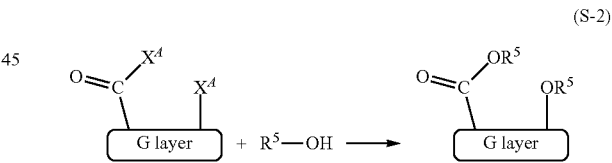

(S-2)

In each of the synthesis schemes (S-1) and (S-2), G layer represents a graphene layer.

In each of the synthesis schemes (S-1) and (S-2), $R^5$ represents a chain group containing an ether bond or an ester bond. Specifically, $R^5$ is represented by the general formulae (R-1) to (R-4) shown above.

In each of the synthesis schemes (S-1) and (S-2), $X^A$ represents halogen. Preferably, $X^A$ is chlorine, bromine, or iodine. Further preferably, $X^A$ is chlorine or bromine.

As shown in the synthesis scheme (S-1), graphene or graphene oxide is made to react with a halide having a chain group containing an ether bond or an ester bond, whereby a chemically modified objective compound can be obtained.

A halide having a chain group containing an ether bond or an ester bond can be obtained by reacting alcohol having a chain group containing an ether bond or an ester bond with thionyl chloride, sulfuryl chloride, phosphorus trichloride, phosphorus pentachloride, phosphorus tribromide, phosphorus pentabromide, hydrogen bromide, hydrogen iodide, cyanuric chloride, or the like.

A chloride having a chain group containing an ether bond or an ester bond can be obtained by reacting alcohol having a chain group containing an ether bond or an ester bond with triphenylphosphine and carbon tetrachloride. A bromide having a chain group containing an ether bond or an ester bond can be obtained by reacting alcohol having a chain group containing an ether bond or an ester bond with triphenylphosphine and carbon tetrabromide. The reaction using triphenylphosphine and carbon tetrachloride or carbon tetrabromide is preferable because the reaction proceeds under neutral conditions and can therefore inhibit decomposition of alcohol having a chain group containing an ether bond or an ester bond.

As shown in the synthesis scheme (S-2), a graphene compound having a halogen group is made to react with alcohol having a chain group containing an ether bond or an ester bond, whereby a chemically modified objective compound can be obtained.

A graphene compound having a halogen group can be obtained by reacting graphene or graphene oxide with thionyl chloride, sulfuryl chloride, phosphorus trichloride, phosphorus pentachloride, phosphorus tribromide, phosphorus pentabromide, hydrogen bromide, hydrogen iodide, cyanuric chloride, or the like.

The reactions shown in the synthesis schemes (S-1) and (S-2) are preferably performed under conditions where water in an air atmosphere is prevented from entering because hydrolysis of a halide or the like can be avoided under such conditions. The reactions may be performed in an atmosphere of an inert gas such as nitrogen or a rare gas such as argon. The atmosphere of the reactions is not limited to nitrogen, argon, or the like and may be an air atmosphere, for example.

Examples of a solvent that can be used in each of the synthesis schemes (S-1) and (S-2) include, but are not limited to, aromatic hydrocarbons such as toluene, xylene, and mesitylene; hydrocarbons such as hexane and heptane; and ether such as ethylene glycol dimethyl ether. However, the solvent that can be used is not limited to these solvents.

Specific Example

Specific examples of alcohol having a chain group containing an ether bond or an ester bond are shown below to describe specific examples of a chain group containing an ether bond or an ester bond. Note that compounds 121 to 147 each have one or more ether bonds. Compounds 150 to 175 each have one or more ester bonds. Compounds 180 to 187 each have an ester bond and an ether bond.

[Chemical formula 22]

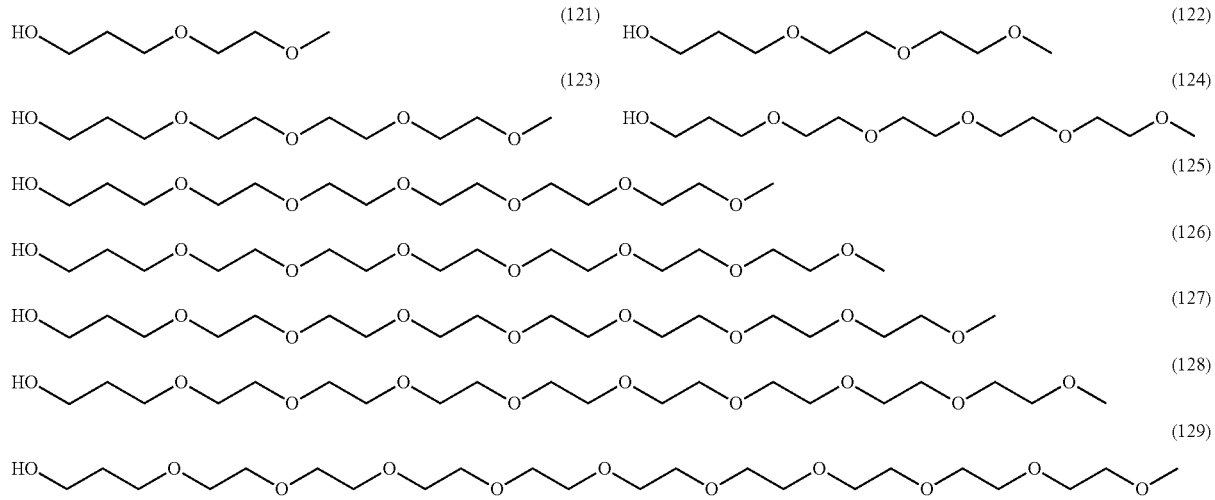

[Chemical formula 23]

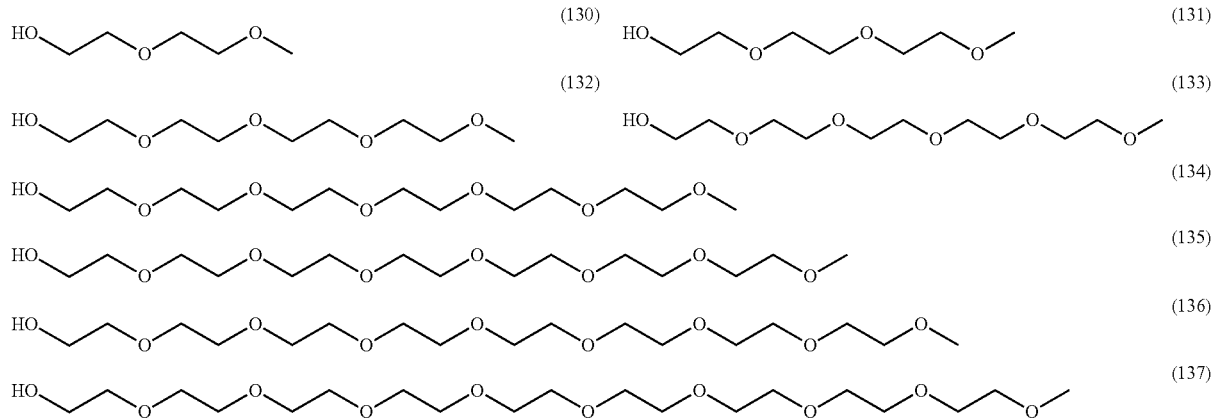

-continued

Chemical structures (138)–(147), (150)–(155) shown.

[Chemical formula 24]

[Chemical formula 25]

-continued

[Chemical formula 26]

[Chemical formula 27]

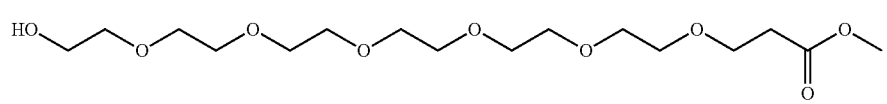 (181)

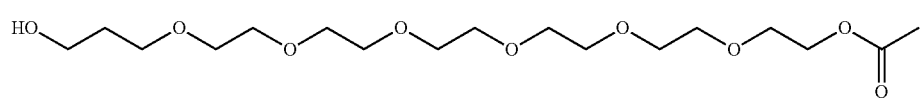 (182)

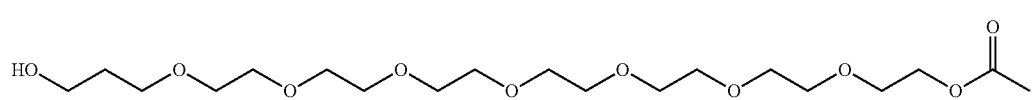 (183)

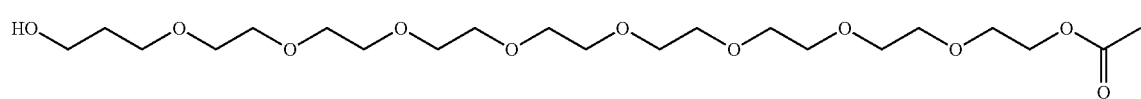 (184)

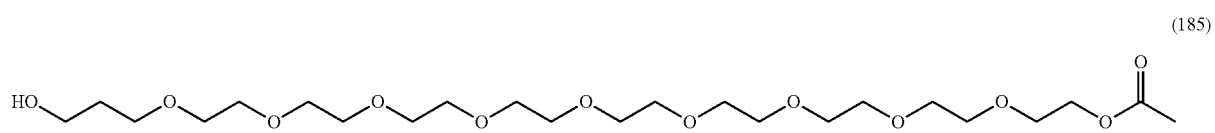 (185)

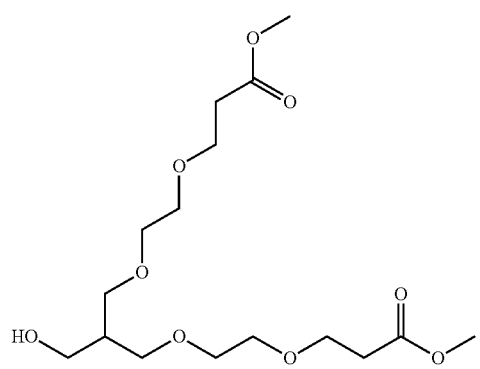 (186)

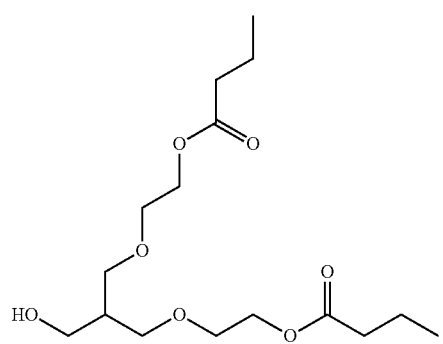 (187)

With the use of any of the above alcohol, the graphene compound that has a chain group containing one or more ether bonds or ester bonds or a chain group containing an ether bond and an ester bond can be formed. The graphene compound chemically modified with any of these alcohols has low electron conductivity and high lithium ion conductivity and thus is suitably used for a solid electrolyte or a separator of a lithium-ion storage battery. Note that the graphene compound of one embodiment of the present invention may be formed without using the above-mentioned alcohols.

Next, specific examples of a formation method of a chemically modified graphene compound of one embodiment of the present invention are described. Here, two examples of a formation method of graphene oxide represented by a structural formula (301) shown below are described.

[Chemical formula 28]

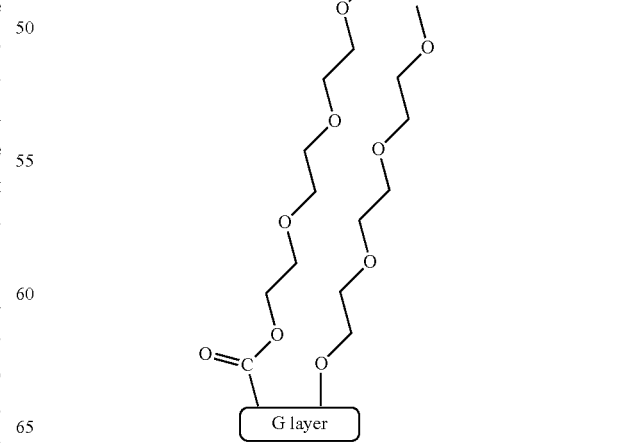 (301)

Specific Example 1 of Formation Method

First, triethylene glycol monomethyl ether, triphenylphosphine (Ph$_3$P), and carbon tetrachloride (CCl$_4$) are put into a flask. This mixture is stirred while heated at approximately 80° C., and then, hexane is put into the flask. The resulting mixture is filtered and a solvent contained in the resulting solution is removed, whereby an objective substance can be obtained. A synthesis scheme (S-3) relating to this formation method is shown below.

[Chemical formula 29]

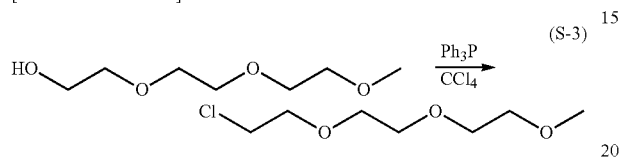

(S-3)

Next, graphene oxide and N,N-dimethylformamide (DMF) are put into a flask. After an ultrasonic wave is sent into the obtained mixture with an ultrasonic cleaning machine for five minutes, the product of the reaction shown in the synthesis scheme (S-3) is added thereto. After the mixture is stirred while heated at approximately 60° C., this mixture is washed with ethanol and pure water, and suction filtration is performed to collect a solid. A solvent contained in the obtained solid is removed under reduced pressure, whereby an objective black powder substance is obtained. A synthesis scheme (S-4) relating to this formation method is shown below.

[Chemical formula 30]

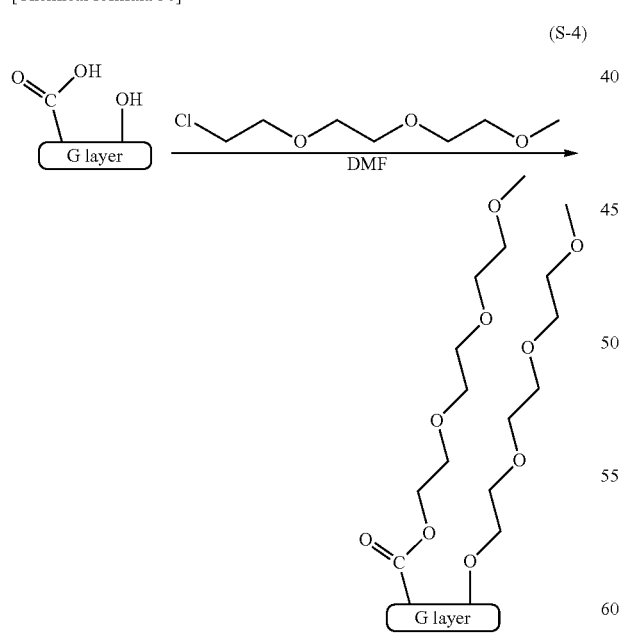

(S-4)

Specific Example 2 of Formation Method

First, graphene oxide, thionyl chloride, and a solvent are put into a flask. After the mixture is stirred, the solvent is removed. Then, triethylene glycol monomethyl ether and DMF are put into the flask. After the obtained mixture is stirred while heated at approximately 60° C., the mixture is washed with ethanol and pure water, and suction filtration is performed to collect a solid. The solvent that remains in the solid is removed under reduced pressure, whereby an objective black powder substance is obtained. Synthesis schemes (S-5) and (S-6) relating to the formation method are shown below.

[Chemical formula 31]

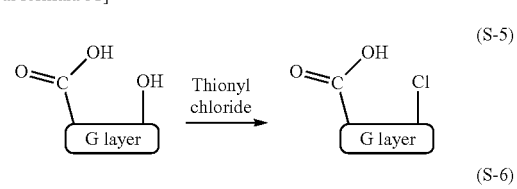

(S-5)

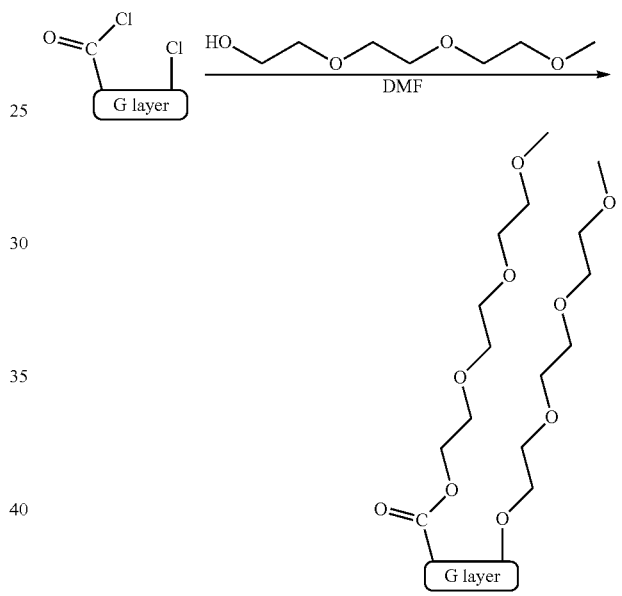

(S-6)

Chemical modification of a graphene compound formed by the formation method of one embodiment of the present invention can be confirmed by Fourier transform infrared spectroscopy (FT-IR) analysis. Interlayer distance in the chemically modified graphene compound of one embodiment of the present invention can be measured by X-ray diffraction (XRD) analysis.

In Embodiment 1, one embodiment of the present invention has been described. Other embodiments of the present invention are described in Embodiments 2 to 5. Note that one embodiment of the present invention is not limited to the above examples. For example, although an example of the graphene compound that has a chain group containing one or more ether bonds or ester bonds or a chain group containing an ether bond and an ester bond is described as one embodiment of the present invention, one embodiment of the present invention is not limited to this example.

This embodiment can be combined with any other embodiment as appropriate.

Embodiment 2

In this embodiment, another example of a graphene compound formed according to one embodiment of the present invention is described. In addition, another example of a method for forming a graphene compound by chemical modification is described.

A graphene compound of one embodiment of the present invention has a sufficient insulating property. It is preferable that a graphene compound be chemically modified to have a bulky substituent, for example. Specifically, the molecular weight of a substituent in a graphene compound is preferably increased. Furthermore, a graphene compound preferably has a substituent having a branch or a plurality of branches. A bulky substituent can effectively increase the distance between a plurality of sheet-like graphene layers, so that a graphene compound can have a sufficient insulating property.

The graphene compound of one embodiment of the present invention has an affinity for lithium ions. For example, the graphene compound is preferably chemically modified to have a substituent containing at least one of an ester bond and an amide bond. The ester bond and the amide bond are classified into a polar group. The ester bond and the amide bond each have an affinity for lithium ions owing to its polarity and can contribute to the dissociation of a lithium salt and the transfer of lithium ions. Furthermore, when the graphene compound is used for a solid electrolyte of a lithium-ion storage battery, the number of ester bonds and amide bonds in a substituent of the graphene compound is preferably large to improve the mobility of lithium ions.

The graphene compound of one embodiment of the present invention may have an ether bond in addition to at least one of the ester bond and the amide bond. The ether bond is classified into a polar group like the ester bond and the amide bond. The ether bond has an affinity for lithium ions owing to its polarity and can contribute to the dissociation of a lithium salt and the transfer of lithium ions.

By the formation method of a graphene compound of one embodiment of the present invention, the molecular weight, the number of branches, the number of ester bonds and amide bonds, or the like of a substituent can be increased as a result of repeating the reaction using the same material. Therefore, the formation method of a graphene compound of one embodiment of the present invention enables easy manufacture of graphene compounds varying in the molecular weight, the number of branches, the number of ester bonds and amide bonds, or the like of a substituent depending on required characteristics. Moreover, when the manufacturing method of a graphene compound of one embodiment of the present invention is used, an increase in material cost can be prevented.

A general formula (G1) for describing a chemically modified graphene compound of one embodiment of the present invention is shown below.

[Chemical formula 32]

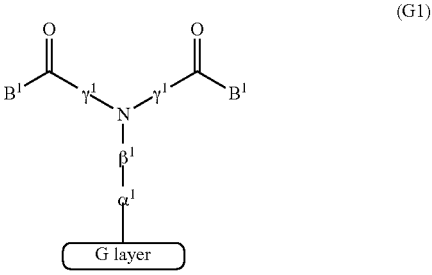

(G1)

In the general formula (G1), G layer represents a graphene layer.

Note that in the graphene compound shown in general formulae, structural formulae, synthesis schemes, or the like in this specification and the like, the graphene layer is bonded to one substituent in some cases, but the kind and the number of substituents bonded to the graphene layer in the present invention are not limited thereto. For example, the graphene layer may be bonded to a plurality of substituents. Furthermore, the graphene layer may have a substituent that is not shown in the general formulae, the structural formulae, the synthesis schemes, or the like.

In the general formula (G1), $\alpha^1$ represents an ether bond, an ester bond, or a bond represented by a general formula ($\alpha$-1) shown below.

[Chemical formula 33]

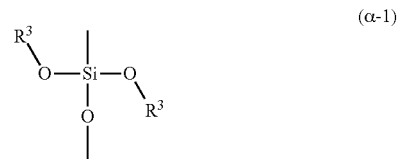

($\alpha$-1)

In the general formula ($\alpha$-1), $R^3$ represents hydrogen or a substituted or unsubstituted alkyl group having 1 to 10 carbon atoms.

In the general formula (G1), $\beta^1$ and $\gamma^1$ each independently represent a substituted or unsubstituted alkylene group having 1 to 10 carbon atoms. Furthermore, $\beta^1$ and $\gamma^1$ may have an ether bond.

In the general formula (G1), $B^1$ has an alkoxy group or an alkylamino group. Specifically, $B^1$ in the general formula (G1) is represented by a general formula (B-1) or a general formula (B-2) shown below.

[Chemical formula 34]

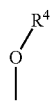

(B-1)

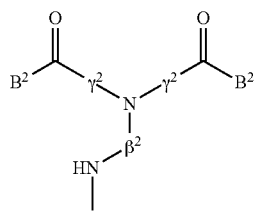
(B-2)

In the general formula (B-1) shown above, $R^4$ represents a substituted or unsubstituted alkyl group having 1 to 10 carbon atoms.

In the general formula (B-2) shown above, $\beta^2$ and $\gamma^2$ each independently represent a substituted or unsubstituted alkylene group having 1 to 10 carbon atoms. Furthermore, $\beta^2$ and $\gamma^2$ may have an ether bond.

In the general formula (B-2) shown above, $B^2$ has an alkoxy group or an alkylamino group. Specifically, $B^2$ is represented by the general formula (B-1) shown above or a general formula (B-3) shown below.

[Chemical formula 35]

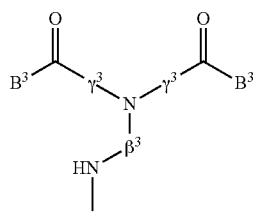
(B-3)

In the general formula (B-3) shown above, $\beta^3$ and $\gamma^3$ each independently represent a substituted or unsubstituted alkylene group having 1 to 10 carbon atoms. Furthermore, $\beta^3$ and $\gamma^3$ may have an ether bond.

In the general formula (B-3) shown above, $B^3$ has an alkoxy group or an alkylamino group. Specifically, $B^3$ is represented by the general formula (B-1) shown above or a general formula (B-4) shown below.

[Chemical formula 36]

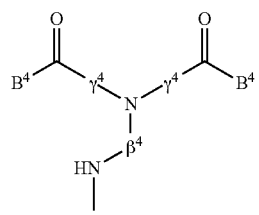
(B-4)

In the general formula (B-4) shown above, $\beta^4$ and $\gamma^4$ each independently represent a substituted or unsubstituted alkylene group having 1 to 10 carbon atoms. Furthermore, $\beta^4$ and $\gamma^4$ may have an ether bond.

In the general formula (B-4) shown above, $B^4$ has an alkoxy group or an alkylamino group. Specifically, $B^4$ is represented by the general formula (B-1) shown above or a general formula (B-5) shown below.

[Chemical formula 37]

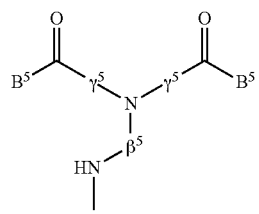
(B-5)

In the general formula (B-5) shown above, $\beta^5$ and $\gamma^5$ each independently represent a substituted or unsubstituted alkylene group having 1 to 10 carbon atoms. Furthermore, $\beta^5$ and $\gamma^5$ may have an ether bond.

In the general formula (B-5) shown above, $B^5$ is represented by the general formula (B-1) shown above.

In a chemically modified graphene compound of one embodiment of the present invention, $B^5$ in the general formula (B-5) shown above may be represented by one of the general formulae (B-2) to (B-5) shown above. That is, a chemically modified graphene compound of one embodiment of the present invention may have a structure where unit structures each represented by any of the general formulae (B-2) to (B-5) are bonded together successively.

Furthermore, a chemically modified graphene compound of one embodiment of the present invention can also be described using general formulae (G3) to (G5) shown below.

[Chemical formula 38]

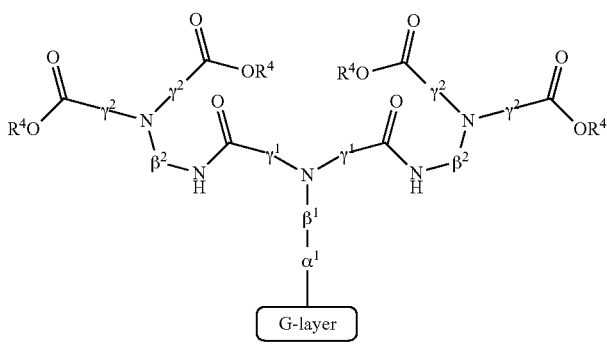
(G3)

-continued (G4)

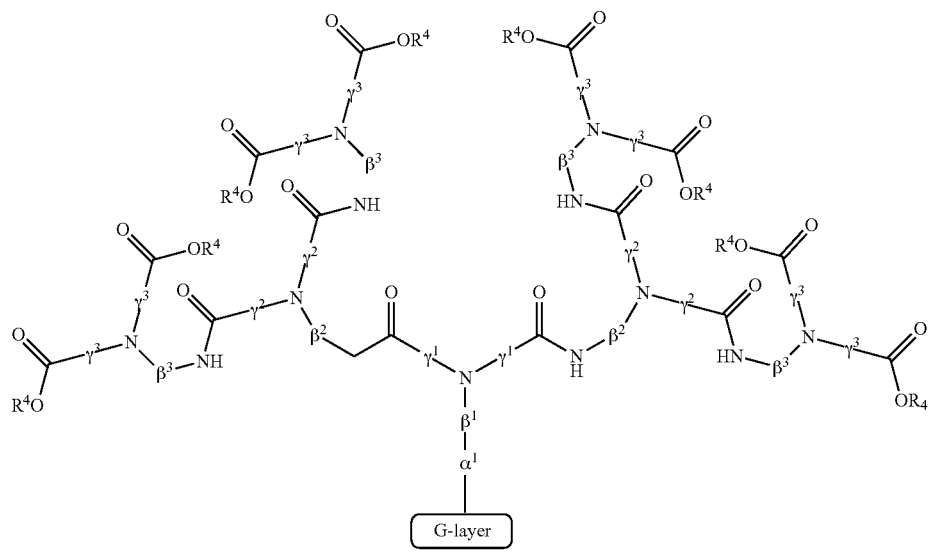

[Chemical formula 39]

(G5)

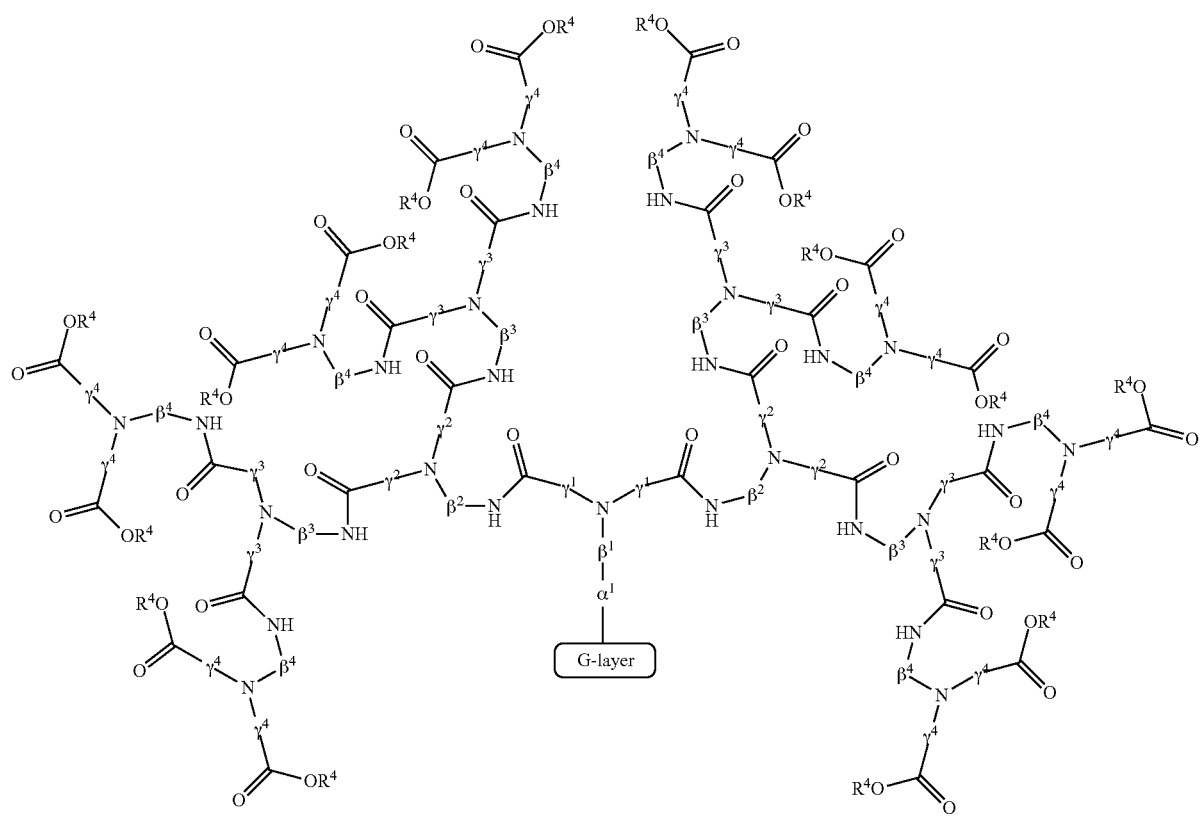

In the general formulae (G3) to (G5), G layer represents a graphene layer as in the above description.

In the general formulae (G3) to (G5), $\alpha^1$ represents an ether bond, an ester bond, or a bond represented by the general formula ($\alpha$-1) as in the above description.

In the general formulae (G3) to (G5), $\beta^1$, $\beta^2$, $\beta^3$, and $\beta^4$ and $\gamma^1$, $\gamma^2$, $\gamma^3$, and $\gamma^4$ each independently represent a substituted or unsubstituted alkylene group having 1 to 10 carbon atoms. Furthermore, $\beta^1$, $\beta^2$, $\beta^3$, and $\beta^4$ and $\gamma^1$, $\gamma^2$, $\gamma^3$, and $\gamma^4$ may have an ether bond.

In the general formulae (G3) to (G5), $R^4$ represents a substituted or unsubstituted alkyl group having 1 to 10 carbon atoms as in the above description.

The molecular weight of a substituent in a chemically modified graphene compound of one embodiment of the present invention is greater than or equal to 200 and less than or equal to 10000. However, when the molecular weight of a substituent is large, the reaction for chemical modification of the graphene compound does not easily proceed. Therefore, preferably, the molecular weight of a substituent in a chemically modified graphene compound of one embodiment of the present invention is greater than or equal to 200 and less than or equal to 6500. Furthermore, it is preferable for a graphene compound to have a substituent with a further increased molecular weight, which leads to an increased insulating property of the graphene compound. Therefore, further preferably, the molecular weight of a substituent in a chemically modified graphene compound of one embodiment of the present invention is greater than or equal to 500 and less than or equal to 6500.

<Chemical Modification>

Next, methods for chemically modifying graphene or graphene oxide to form a chemically modified graphene compound are described.

Methods for forming a graphene compound are described using synthesis schemes (T-1) to (T-11). In the synthesis schemes (T-1) to (T-11), G layer represents a graphene layer as in the above description. In the synthesis schemes (T-1) to (T-11), $\alpha^1$ represents an ether bond, an ester bond, or a bond represented by the general formula ($\alpha$-1) as in the above description. In the synthesis schemes (T-1) to (T-11), $B^1$ is represented by the general formula (B-1) or (B-2) shown above.

In the synthesis schemes (T-1) to (T-11), $\beta^1$ and $\beta^2$ each independently represent a substituted or unsubstituted alkylene group having 1 to 10 carbon atoms as in the above description. In the synthesis schemes (T-1) to (T-11), $\gamma^1$ each independently represent a substituted or unsubstituted alkylene group having 1 to 10 carbon atoms as in the above description. In the synthesis schemes (T-1) to (T-11), $R^4$ represents a substituted or unsubstituted alkyl group having 1 to 10 carbon atoms as in the above description.

First, two different methods for forming the graphene compound represented by the general formula (G1) shown above are described using the synthesis schemes (T-1) and (T-2) shown below.

[Method 1 for Forming Graphene Compound]

A method for forming the graphene compound represented by the general formula (G1) shown above is described using the synthesis scheme (T-1).

[Chemical formula 40]

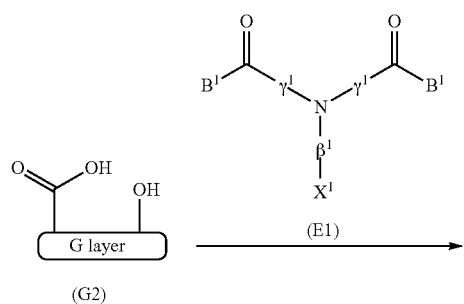

(T-1)

-continued

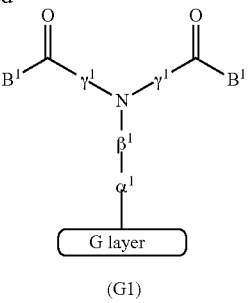

(G1)

In the synthesis scheme (T-1), $X^1$ represents halogen such as chlorine, bromine, or iodine, a trialkoxysilyl group, or a trichlorosilyl group.

As shown in the synthesis scheme (T-1), the graphene oxide represented by the general formula (G2) is made to react with a compound represented by a general formula (E1), whereby the graphene compound represented by the general formula (G1) can be obtained.

A specific synthesis method that uses the synthesis method shown in the synthesis scheme (T-1) is described here. First, graphene oxide, the compound represented by the general formula (E1), and a solvent are put into a reaction container such as a flask. After the mixture is stirred, suction filtration is performed to collect a residue, so that the graphene compound represented by the general formula (G1) can be obtained.

In the case where $X^1$ represents halogen such as chlorine, bromine, or iodine in the synthesis scheme (T-1), a graphene compound where $\alpha^1$ in the general formula (G1) represents an ether bond or an ester bond can be obtained. In other words, in the case where $X^1$ represents halogen such as chlorine, bromine, or iodine in the synthesis scheme (T-1), graphene oxide having both a substituent where $\alpha^1$ represents an ether bond and a substituent where $\alpha^1$ represents an ester bond is obtained. Specifically, when a hydroxy group in graphene oxide reacts with the compound represented by the general formula (E1), an ether bond is formed as $\alpha^1$. When a carboxyl group in graphene oxide reacts with the compound represented by the general formula (E1), an ester bond is formed as $\alpha^1$.

Note that in the case where $X^1$ represents halogen such as chlorine, bromine, or iodine in the synthesis scheme (T-1), a reaction in which an ester bond is formed as $\alpha^1$ might be promoted by adding a base such as potassium carbonate, for example.

In the case where $X^1$ represents a trialkoxysilyl group or a trichlorosilyl group in the synthesis scheme (T-1), a graphene compound where $\alpha^1$ in the general formula (G1) is represented by the general formula ($\alpha$-1) shown above can be obtained. In such a case, an objective compound can be obtained by adding a Lewis base. Such a reaction is referred to as silylation in some cases.

Silylation means the substitution of a silicon atom for a hydrogen atom in a hydroxy group, an amino group, a carboxyl group, an amide group, a mercapto group, or the like. A silicon compound used for silylation is referred to as a silylating agent in some cases.

As the Lewis base, alkylamine or a heterocyclic aromatic compound is used. Specifically, one or more of butylamine, pentylamine, hexylamine, diethylamine, dipropylamine, dibutylamine, triethylamine, tripropylamine, and pyridine is used.

[Method 2 for Forming Graphene Compound]

A method for forming the graphene compound represented by the general formula (G1) shown above is described using the synthesis scheme (T-2).

[Chemical formula 41]

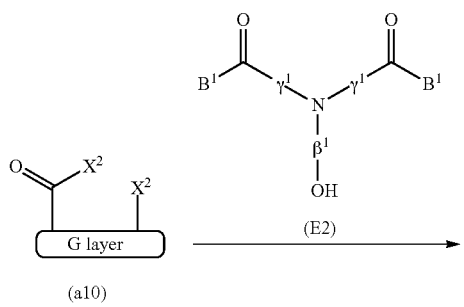

In the synthesis scheme (T-2), $X^2$ represents halogen such as chlorine, bromine, or iodine.

In the synthesis scheme (T-2), $\alpha^2$ represents an ester bond or an ether bond.

As shown in the synthesis scheme (T-2), a graphene compound (a10) having a halogen group is made to react with a compound (E2), whereby a graphene compound represented by the general formula (G1) can be obtained.

Note that a graphene compound having a halogen group can be obtained by reacting graphene or graphene oxide with thionyl chloride, sulfuryl chloride, phosphorus trichloride, phosphorus pentachloride, phosphorus tribromide, phosphorus pentabromide, hydrogen bromide, hydrogen iodide, cyanuric chloride, or the like.

Next, as more specific examples, two different methods for forming a graphene compound represented by a general formula (G6) shown below are described.

[Chemical formula 42]

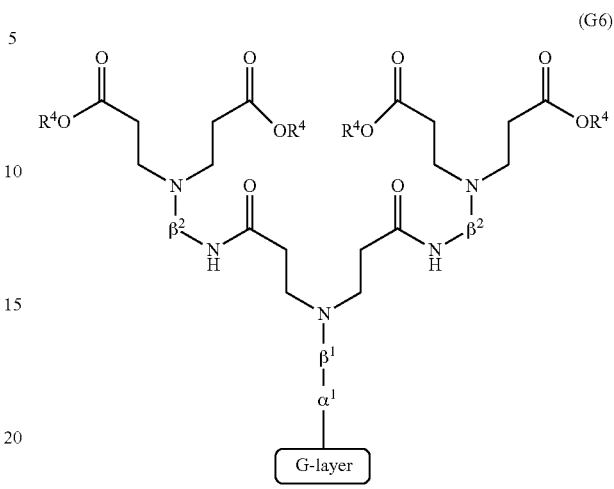

The graphene compound represented by the general formula (G6) has a structure where $\gamma^1$ and $\gamma^2$ are each an ethylene group in the general formula (G3).

In the general formula (G6), G layer represents a graphene layer as in the above description.

In the general formula (G6), $\alpha^1$ represents an ether bond, an ester bond, or a bond represented by the general formula ($\alpha$-1) shown above as in the above description.

In the general formula (G6), $\beta^1$ and $\beta^2$ each independently represent a substituted or unsubstituted alkylene group having 1 to 10 carbon atoms and $\beta^1$ and $\beta^2$ may each have an ether bond, as in the above description.

In the general formula (G6), $R^4$ represents a substituted or unsubstituted alkyl group having 1 to 10 carbon atoms as in the above description.

[Method 3 for Forming Graphene Compound]

A method for forming the graphene compound represented by the general formula (G6) is described using the synthesis schemes (T-3) to (T-7).

[Chemical formula 43]

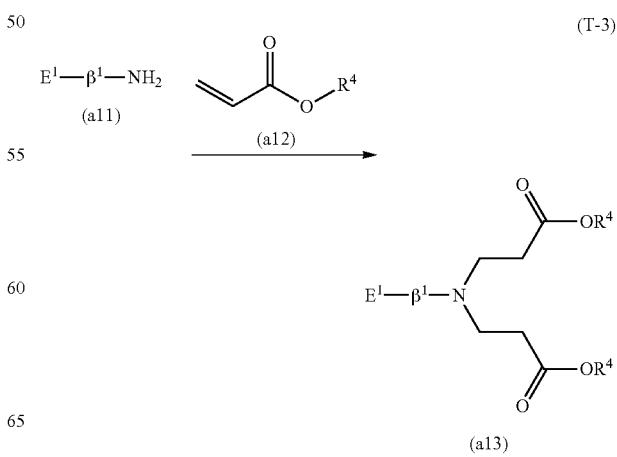

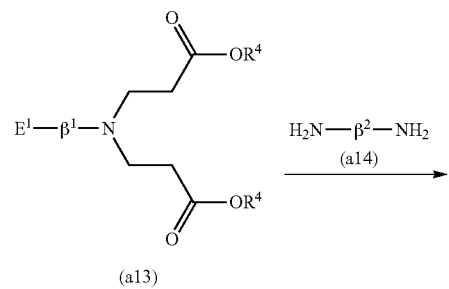
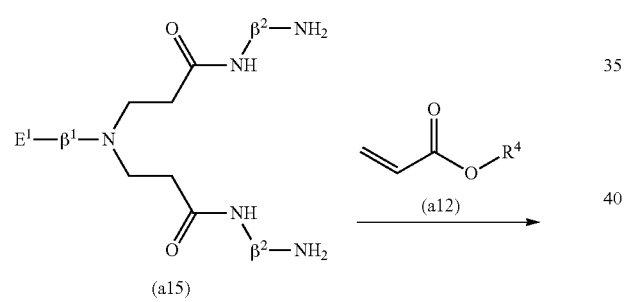
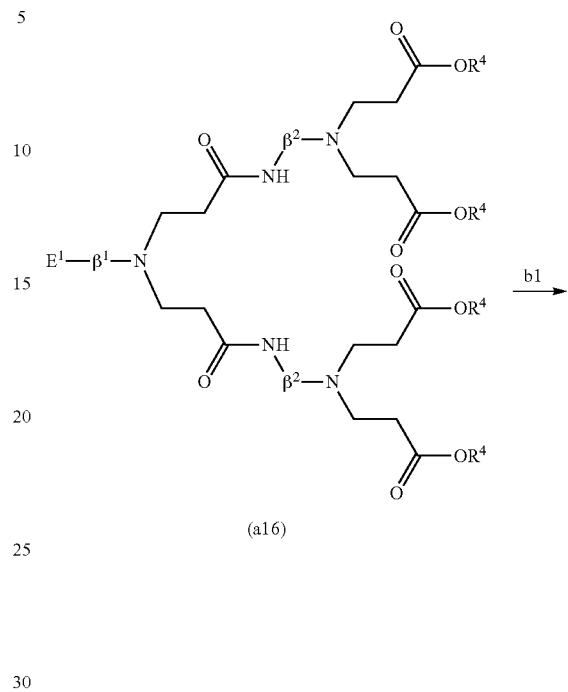
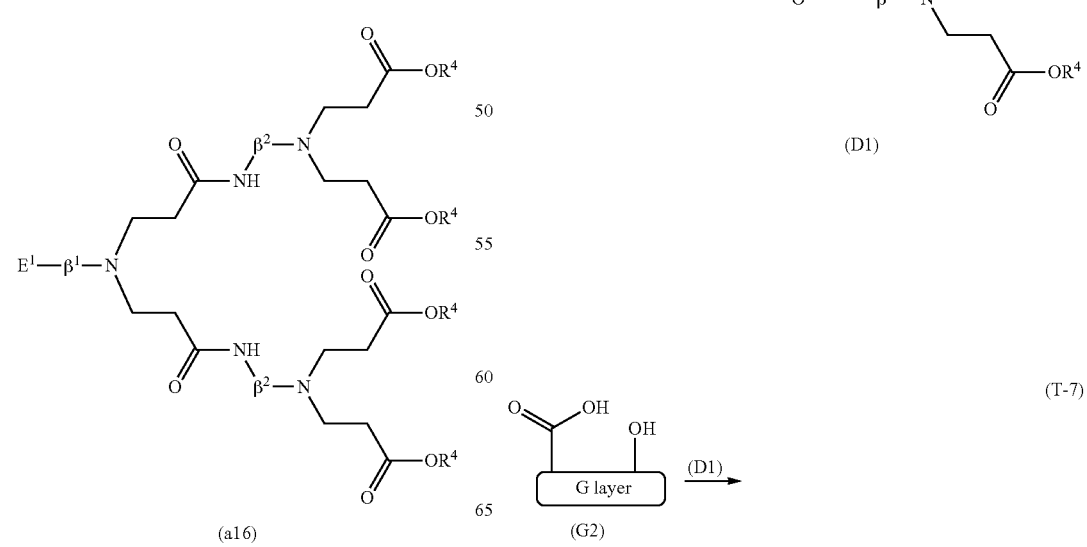
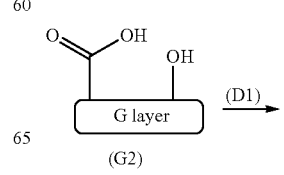

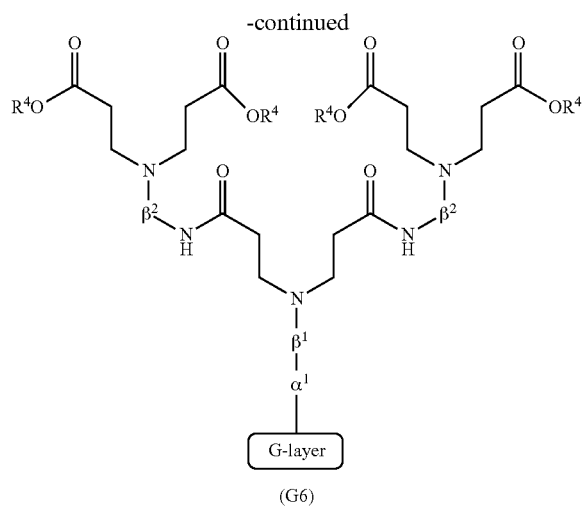

(G6)

In each of the synthesis schemes (T-3) to (T-6), $E^1$ represents a hydroxyl group or a trialkoxysilyl group such as a trimethoxysilyl group or a triethoxysilyl group.

In the synthesis scheme (T-6), X represents halogen such as chlorine, bromine, or iodine, a trialkoxysilyl group, or a trichlorosilyl group.

First, as shown in the synthesis scheme (T-3), a compound (a11) is made to react with an acrylic ester compound (a12), whereby a compound (a13) can be obtained. As the acrylic ester compound (a12), methyl acrylate, ethyl acrylate, butyl acrylate, or the like can be used, for example.

Then, as shown in the synthesis scheme (T-4), the compound (a13) is made to react with a diamine compound (a14), whereby a compound (a15) can be obtained. As the diamine compound (a14), alkyldiamine such as ethylenediamine or tetramethylenediamine can be used, for example.

Then, as shown in the synthesis scheme (T-5), the compound (a15) is made to react with the acrylic ester compound (a12), whereby a compound (a16) can be obtained.

Then, as shown in the synthesis scheme (T-6), the compound (a16) is made to react with a reagent b1, whereby a compound represented by a general formula (D1) can be obtained. As the reagent b1, thionyl chloride, sulfuryl chloride, phosphorus trichloride, phosphorus pentachloride, phosphorus tribromide, phosphorus pentabromide, hydrogen bromide, hydrogen iodide, cyanuric chloride, or the like can be used. Alternatively, as the reagent b1, triphenylphosphine and carbon tetrachloride or carbon tetrabromide can be used in combination.

Note that when $E^1$ in the compound (a16) is a hydroxyl group, it is preferable to use triphenylphosphine and carbon tetrachloride or carbon tetrabromide in combination as the reagent b1.

When $E^1$ in the compound (a16) is a trialkoxysilyl group such as a trimethoxysilyl group or a triethoxysilyl group, it is preferable to use thionyl chloride as the reagent b1.

Finally, as shown in the synthesis scheme (T-7), the graphene oxide represented by the general formula (G2) is made to react with the compound represented by the general formula (D1), whereby the graphene compound represented by the general formula (G6) can be obtained.

In the synthesis scheme (T-7), a graphene compound where $\alpha^1$ in the general formula (G6) represents an ether bond or an ester bond can be obtained in the case where X represents halogen such as chlorine, bromine, or iodine. In other words, in the synthesis scheme (T-7), graphene oxide having both a substituent where $\alpha^1$ represents an ether bond and a substituent where $\alpha^1$ represents an ester bond is obtained in the case where X represents halogen such as chlorine, bromine, or iodine. Specifically, when a hydroxy group in graphene oxide reacts with the compound represented by the general formula (D1), an ether bond is formed as $\alpha^1$. When a carboxyl group in graphene oxide reacts with the compound represented by the general formula (D1), an ester bond is formed as $\alpha^1$.

Note that in the case where X represents halogen such as chlorine, bromine, or iodine in the synthesis scheme (T-7), a reaction in which an ester bond is formed as $\alpha^1$ might be promoted by adding a base such as potassium carbonate, for example.

In the case where X represents a trialkoxysilyl group or a trichlorosilyl group in the synthesis scheme (T-7), a graphene compound where $\alpha^1$ in the general formula (G6) is represented by the general formula ($\alpha$-1) shown above can be obtained. In such a case, an objective compound can be obtained by adding a Lewis base.

As the Lewis base, alkylamine or a heterocyclic aromatic compound is used. Specifically, one or more of butylamine, pentylamine, hexylamine, diethylamine, dipropylamine, dibutylamine, triethylamine, tripropylamine, and pyridine is used.

By increasing the number of steps in this formation method, the molecular weight, the number of branches, the number of ester bonds and amide bonds, or the like of a substituent of a graphene compound can be increased. For example, after the compound (a16) is made to react with the diamine compound (a14) as in the synthesis scheme (T-4), the obtained compound is made to react with the acrylic ester compound (a12) as in the synthesis scheme (T-5). In the synthesized compound, the molecular weight, the number of branches, and the number of ester bonds and amide bonds are larger than those of the compound (a16).

Furthermore, the compound is made to react with the reagent b1 as in the synthesis scheme (T-6), and then the obtained compound is made to react with graphene oxide as in the synthesis scheme (T-7). The molecular weight, the number of branches, and the number of ester bonds and amide bonds of a substituent of the resulting graphene compound are larger than those of the graphene compound represented by the general formula (G6). Specifically, a graphene compound having a structure where $\beta^3$ is the same as $\beta^2$ and $\gamma^1$, $\gamma^2$, and $\gamma^3$ are ethylene groups in the general formula (G4) can be obtained.

Note that the synthesis scheme (T-3) shown above shows the method for obtaining the compound (a13) using the acrylic ester compound (a12), but the method for obtaining the compound (a13) is not limited thereto. For example, the compound (a13) can be obtained also by reacting, with the compound (a11), a compound where $\gamma''$ is an ethylene group in a general formula (a17) shown below.

The synthesis scheme (T-5) shown above shows the method for obtaining the compound (a16) using the acrylic ester compound (a12), but the method for obtaining the compound (a16) is not limited thereto. For example, the compound (a16) can be obtained also by reacting the compound (a17) shown below with the compound (a15).

[Chemical formula 45]

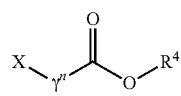
(a17)

In the compound (a17), X represents halogen such as chlorine, bromine, or iodine.

In the compound (a17), $R^4$ represents a substituted or unsubstituted alkyl group having 1 to 10 carbon atoms.

In the compound (a17), $\gamma''$ represents a substituted or unsubstituted alkylene group having 1 to 10 carbon atoms.

When $\gamma''$ is an ethylene group in the compound (a17), reaction of the compound (a17) with the compound (a15) provides the compound (a13).

In this formation method, the formation method of the graphene compound represented by the general formula (G6) is described as an example, but a graphene compound that can be formed by this formation method is not limited to the graphene compound represented by the general formula (G6). For example, a compound where $\gamma^1$ and $\gamma^2$ are alkylene groups other than ethylene groups in the general formula (G3) can be synthesized by using the compound (a17) in the synthesis schemes (T-3), (T-5), and the like shown above.

[Method 4 for Forming Graphene Compound]

A method for forming the graphene compound represented by the general formula (G6) is described using the synthesis schemes (T-8) to (T-11).

[Chemical formula 46]

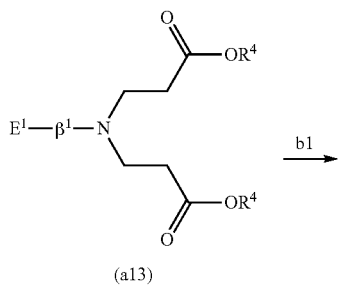
(T-8)
(a13)

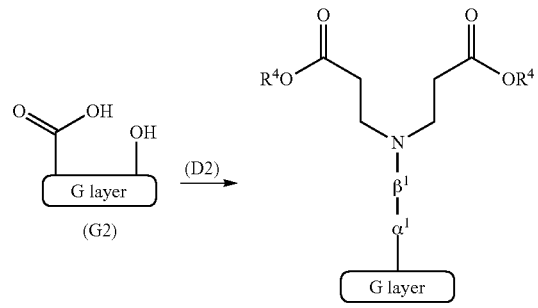
(T-9)
(G2) (a22)

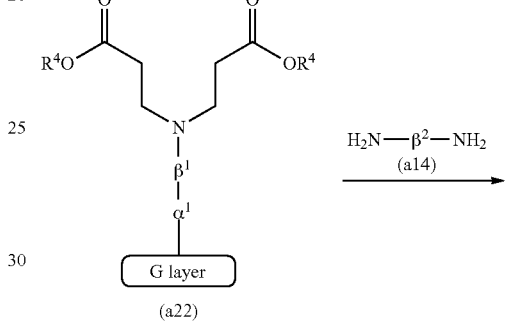
(T-10)
(a22)

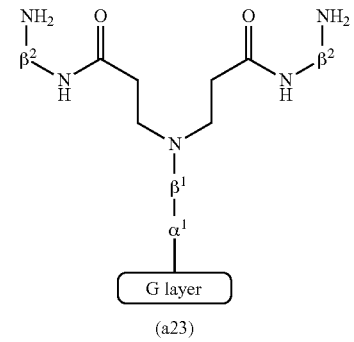
(a23)

[Chemical formula 47]

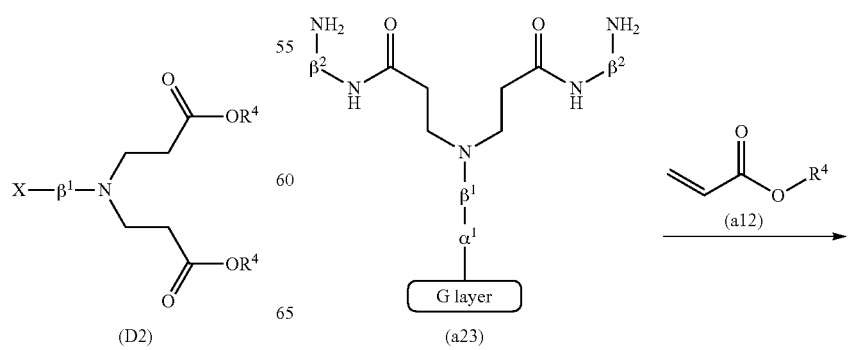
(T-11)
(D2) (a23)

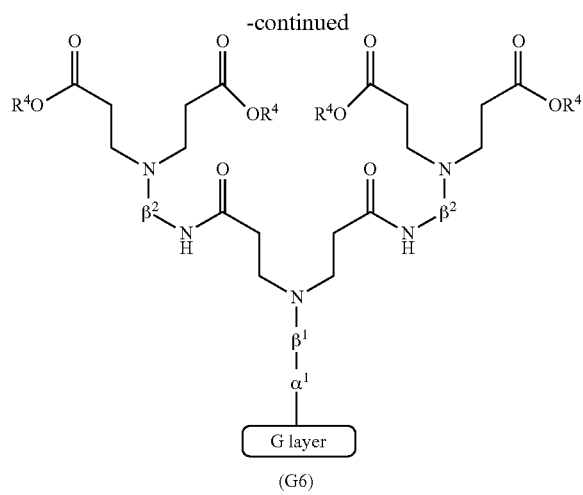

(G6)

In the synthesis scheme (T-8), $E^1$ represents a hydroxyl group or a trialkoxysilyl group such as a trimethoxysilyl group or a triethoxysilyl group as in the above description.

In the synthesis scheme (T-8), X represents halogen such as fluorine, chlorine, bromine, or iodine, a trialkoxysilyl group, or a trichlorosilyl group.

First, as shown in the synthesis scheme (T-8), the compound (a13) is made to react with the reagent b1, whereby the compound represented by the general formula (D2) can be obtained. A reagent that can be used as the reagent b1 is as described above.

Then, as shown in the synthesis scheme (T-9), the graphene oxide represented by the general formula (G2) is made to react with the compound represented by the general formula (D2), whereby a graphene compound (a22) can be obtained.

Note that in the synthesis scheme (T-9), the graphene compound (a22) where $\alpha^1$ represents an ester bond can be selectively obtained by adding a base such as potassium carbonate in the case where X represents halogen such as chlorine, bromine, or iodine.

In the synthesis scheme (T-9), an objective compound can be obtained by adding a Lewis base in the case where X is a trialkoxysilyl group or a trichlorosilyl group.

As the Lewis base, alkylamine or a heterocyclic aromatic compound is used. Specifically, one or more of butylamine, pentylamine, hexylamine, diethylamine, dipropylamine, dibutylamine, triethylamine, tripropylamine, and pyridine is used.

Then, as shown in the synthesis scheme (T-10), the graphene compound (a22) is made to react with the diamine compound (a14), whereby a graphene compound (a23) can be obtained.

Then, as shown in the synthesis scheme (T-11), the graphene compound (a23) is made to react with the acrylic ester compound (a12), whereby a graphene compound represented by the general formula (G6) can be obtained.

A specific synthesis method that uses the synthesis method shown in the synthesis schemes (T-10) and (T-11) is described here.

First, the graphene compound (a22), the diamine compound (a14), and a solvent are put into a reaction container such as a flask. After the mixture is stirred, suction filtration is performed to collect a residue, so that the graphene compound (a23) can be obtained.

Then, the graphene compound (a23), the acrylic ester compound (a12), and a solvent are put into a reaction container such as a flask. After the mixture is stirred, suction filtration is performed to collect a residue, so that the graphene compound represented by the general formula (G6) can be obtained.

By increasing the number of steps in this formation method, the molecular weight, the number of branches, the number of ester bonds and amide bonds, or the like of a substituent of a graphene compound can be increased. For example, after the graphene compound represented by the general formula (G6) is made to react with the diamine compound (a14) as in the synthesis scheme (T-10), the obtained compound is made to react with the acrylic ester compound (a12) as in the synthesis scheme (T-11). Thus, the molecular weight, the number of branches, and the number of ester bonds and amide bonds of a substituent of the resulting graphene compound can be increased. Specifically, a graphene compound having a structure where $\beta^3$ is the same as $\beta^2$ and $\gamma^1$ to $\gamma^3$ are ethylene groups in the general formula (G4) can be obtained.

Specific Example

To describe specific examples of a graphene compound having a substituent containing at least one of an ester bond and an amide bond, specific examples of a compound represented by the general formula (D1) or the general formula (D2) in the synthesis schemes (T-3) to (T-10) are shown below.

[Chemical formula 48]

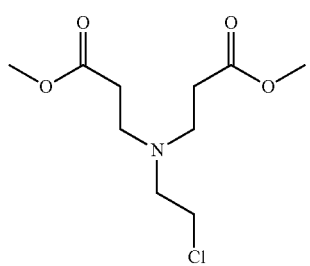
(301)

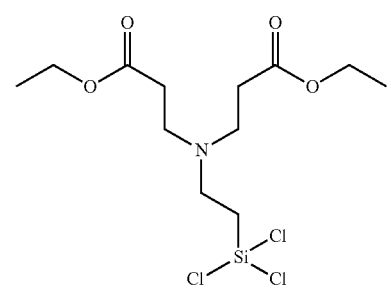
(302)

-continued
(303) 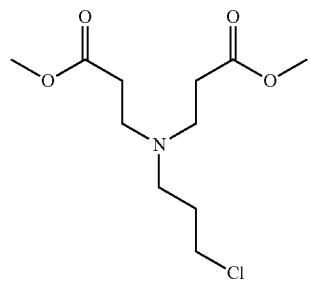
(304) 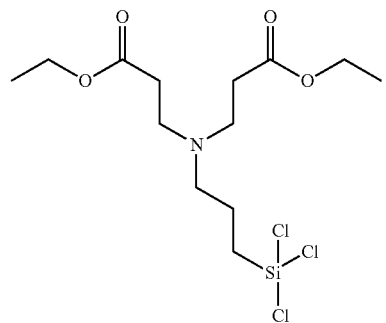
(305) 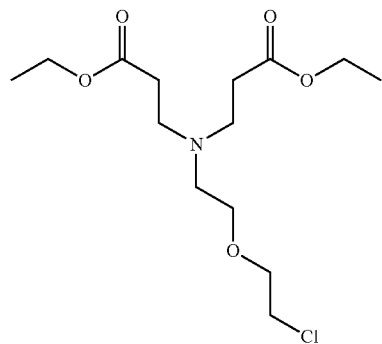
(306) 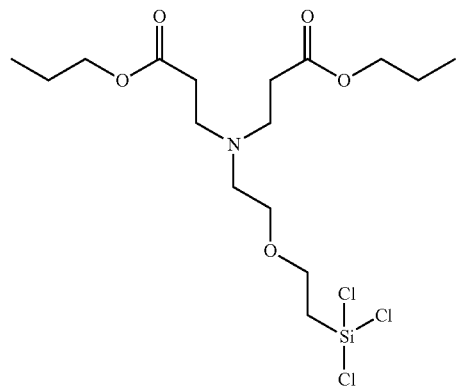
(307) 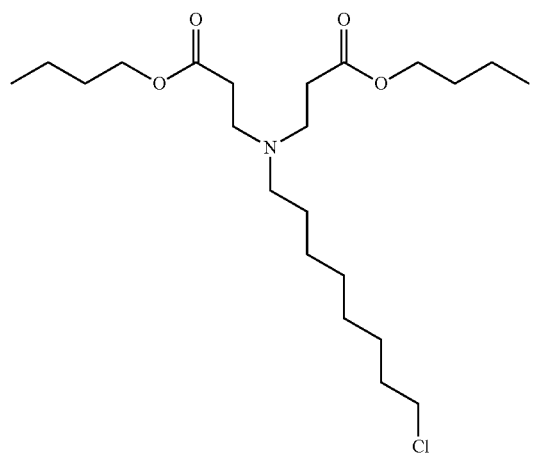
(308) 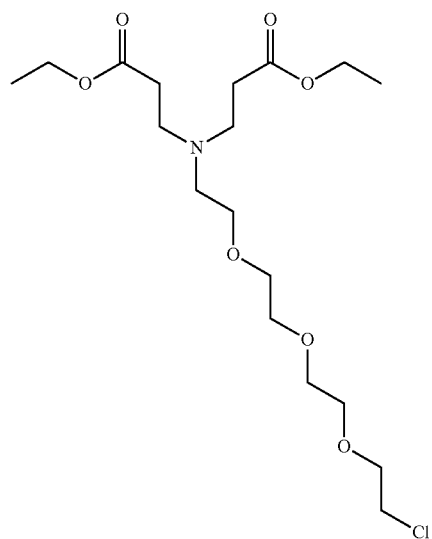

(309)
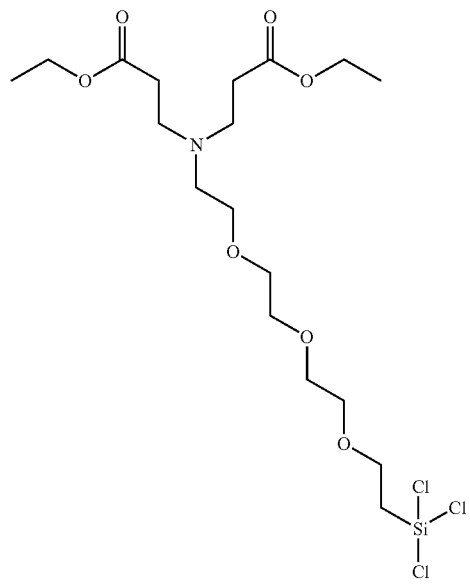
(310)
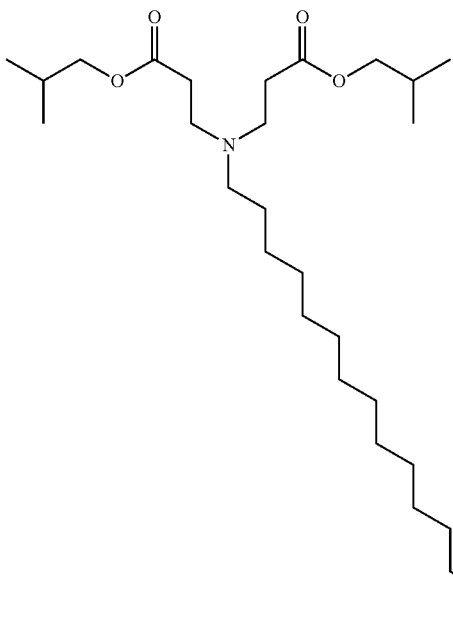
[Chemical formula 49]
(311) (312)
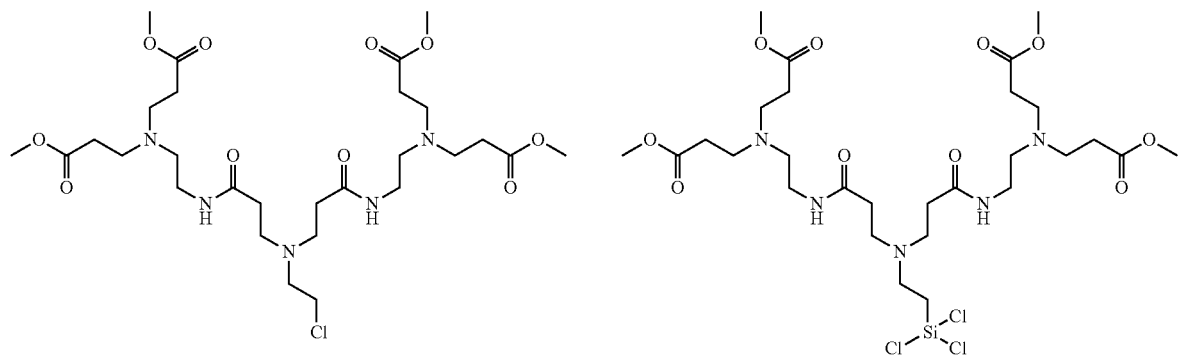
(313)
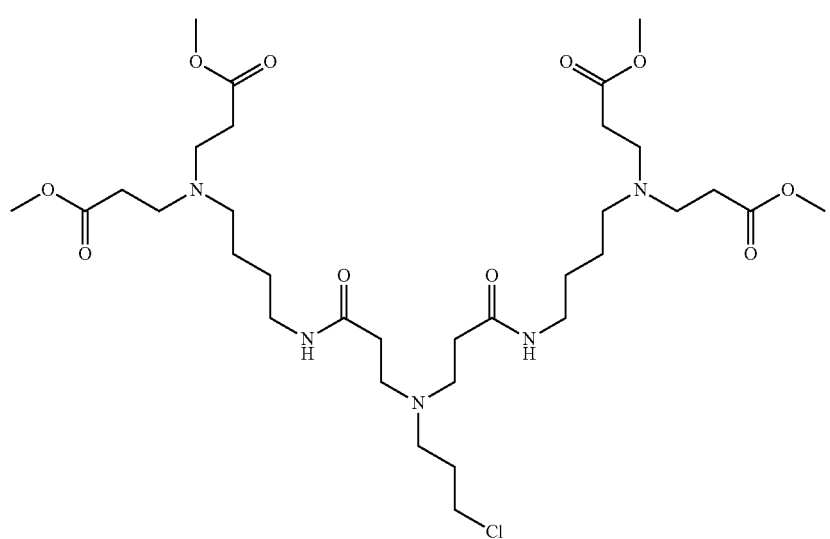

-continued
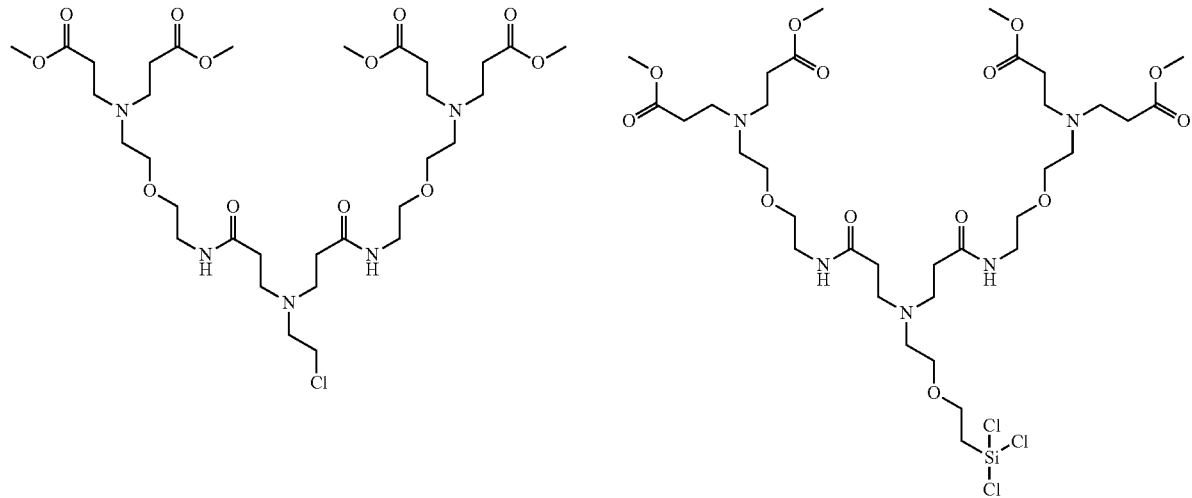
(314)
(315)
[Chemical formula 50]
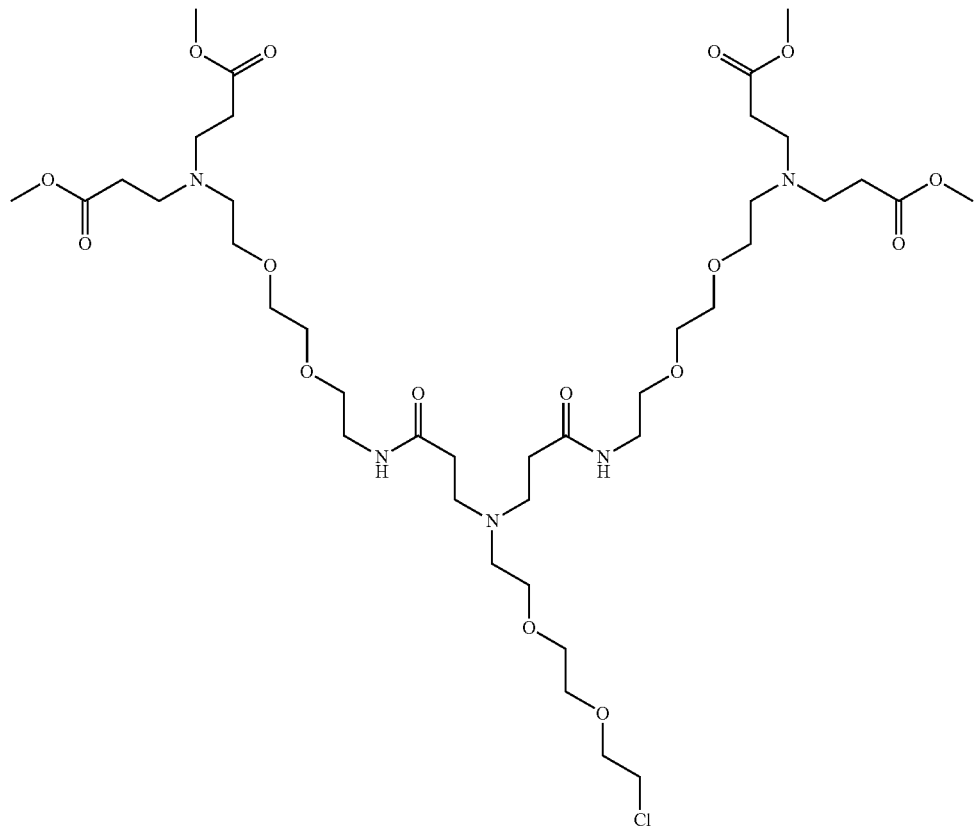
(316)

-continued (317)

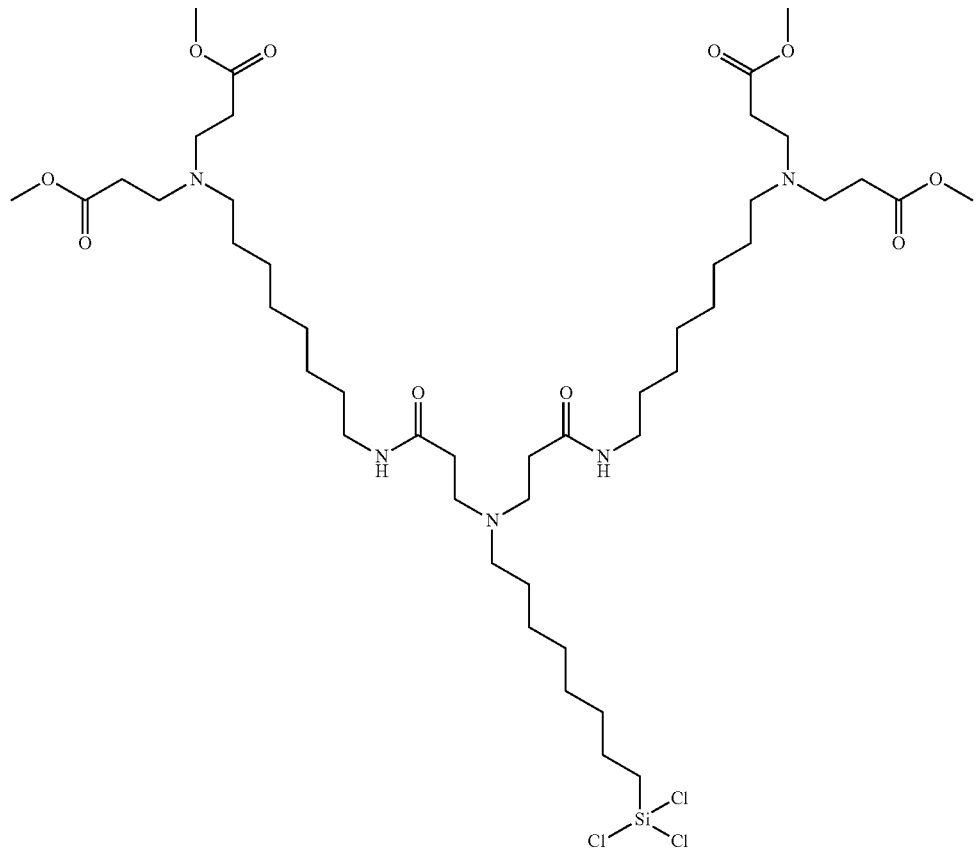

Using any of these compounds enables formation of a graphene compound having a chain group containing at least one of an ester bond and an amide bond. The graphene compound chemically modified with any of these compounds has low electron conductivity and high lithium ion conductivity and thus is suitably used for a solid electrolyte or a separator of a lithium-ion storage battery. Note that the graphene compound of one embodiment of the present invention may be formed without using any of the above-mentioned compounds.

In Embodiment 2, one embodiment of the present invention has been described. Other embodiments of the present invention are described in Embodiment 1 and Embodiments 3 to 5. Note that one embodiment of the present invention is not limited to these. For example, although an example of the graphene compound that has a chain group containing one or more ester bonds and amide bonds is described as one embodiment of the present invention, one embodiment of the present invention is not limited to this example.

This embodiment can be combined with any other embodiment as appropriate.

Embodiment 3

In this embodiment, a structure of a lithium-ion storage battery is described as a power storage device including the graphene compound of one embodiment of the present invention.

Figure 1B:
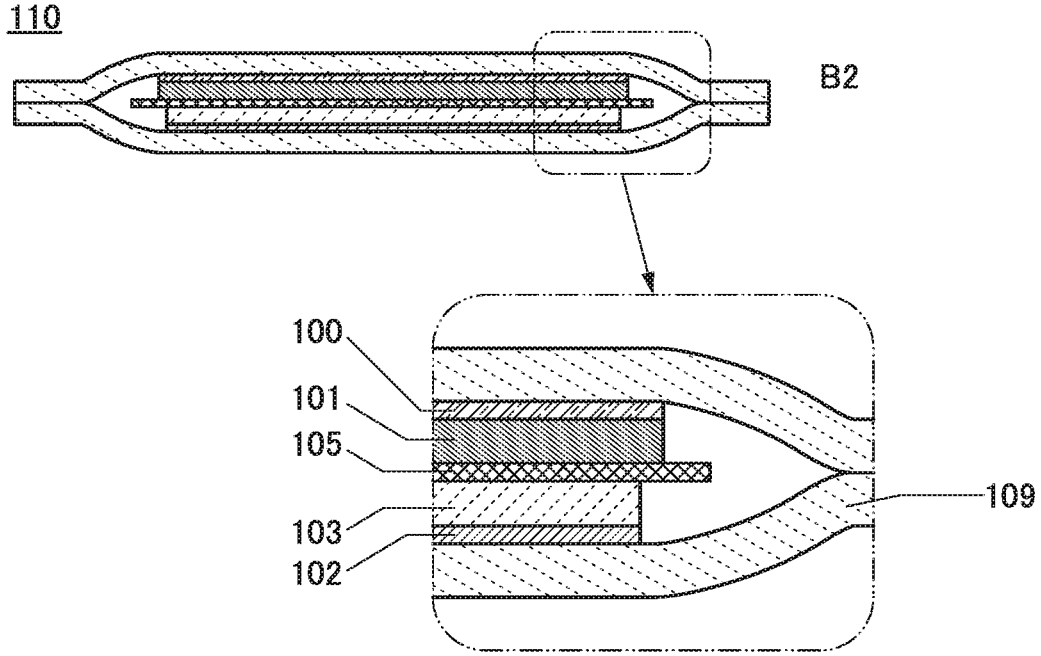

A method for forming a lithium-ion storage battery 110 of one embodiment of the present invention is described below with reference to FIGS. 1A and 1B. FIG. 1A is an external view of the lithium-ion storage battery 110. FIG. 1B is a cross-sectional view taken along dashed-dotted line B1-B2 in FIG. 1A. FIG. 1B is also a schematic cross-sectional view in which a positive electrode current collector 100, a positive electrode active material layer 101, a graphene compound 105 that is a solid electrolyte layer, a negative electrode active material layer 103, and a negative electrode current collector 102 are stacked and enclosed by an exterior body 109. Note that the active material layers can be formed on both surfaces of the current collector, so that the lithium-ion storage battery can have a stacked-layer structure.

<<Structure of Positive Electrode>>

The positive electrode is described. The positive electrode includes the positive electrode active material layer 101 and the positive electrode current collector 100.

As the positive electrode active material used for the positive electrode active material layer 101, a material into and from which carrier ions such as lithium ions can be inserted and extracted can be used. Examples of the material include a lithium-containing material with an olivine crystal structure, a layered rock-salt crystal structure, and a spinel crystal structure.

Typical examples of the lithium-containing material with an olivine crystal structure (general formula: $LiMPO_4$ (M is Fe(II), Mn(II), Co(II), or Ni(II))) include $LiFePO_4$, $LiNiPO_4$, $LiCoPO_4$, $LiMnPO_4$, $LiFe_aNi_bPO_4$, $LiFe_aCo_bPO_4$, $LiFe_aMn_bPO_4$, $LiNi_aCo_bPO_4$, $LiNi_aMn_bPO_4$ ($a+b\leq1$, $0<a<1$, and $0<b<1$), $LiFe_cNi_dCo_ePO_4$, $LiFe_cNi_dMn_ePO_4$, $LiNi_cCo_dMn_ePO_4$ ($c+d+e\leq1$, $0<c<1$, $0<d<1$, and $0<e<1$), and $LiFe_fNi_gCo_hMn_iPO_4$ ($f+g+h+i\leq1$, $0<f<1$, $0<g<1$, $0<h<1$, and $0<i<1$).

For example, lithium iron phosphate ($LiFePO_4$) is preferable because it properly has properties necessary for the positive electrode active material, such as safety, stability, high capacity density, high potential, and the existence of lithium ions which can be extracted in initial oxidation (charging).

Examples of the lithium-containing material with a layered rock-salt crystal structure include lithium cobalt oxide ($LiCoO_2$), $LiNiO_2$, $LiMnO_2$, $Li_2MnO_3$, an NiCo-containing material (the general formula thereof is $LiNi_xCo_{1-x}O_2$ (0<x<1)) such as $LiNi_{0.8}Co_{0.2}O_2$, an NiMn-containing material (the general formula thereof is $LiNi_xMn_{1-x}O_2$ (0<x<1)) such as $LiNi_{0.5}Mn_{0.5}O_2$, and an NiMnCo-containing material (also referred to as NMC, and the general formula thereof is $LiNi_xMn_yCo_{(1-x-y)}O_2$ (x>0, y>0, x+y<1)) such as $LiNi_{1/3}Mn_{1/3}Co_{1/3}O_2$. Moreover, $Li(Ni_{0.8}Co_{0.15}Al_{0.05})O_2$, $Li_2MnO_3$—$LiMO_2$ (M=Co, Ni, or Mn), and the like can be given.

In particular, $LiCoO_2$ is preferable because it has high capacity and higher stability in the air and higher thermal stability than $LiNiO_2$, for example.

Examples of the lithium-containing material with a spinel crystal structure include $LiMn_2O_4$, $Li_{(1+x)}Mn_{(2-x)}O_4$ (0<x<2), $LiMn_{2-x}Al_xO_4$ (0<x<2), and $LiMn_{1.5}Ni_{0.5}O_4$.

It is preferred that a small amount of lithium nickel oxide ($LiNiO_2$ or $LiNi_{(1-x)}M_xO_2$ (M=Co, Al, or the like), (0<x<1)) be added to the lithium-containing material with a spinel crystal structure that contains manganese, such as $LiMn_2O_4$, in which case the dissolution of manganese and the decomposition of an electrolyte can be suppressed, for example.

A composite oxide represented by a general formula $Li_{(2-j)}MSiO_4$ (M is Fe(II), Mn(II), Co(II), or Ni(II), $0 \leq j \leq 2$) can also be used as the positive electrode active material. Typical examples of $Li_{(2-j)}MSiO_4$ (general formula) are $Li_{(2-j)}FeSiO_4$, $Li_{(2-j)}CoSiO_4$, $Li_{(2-j)}MnSiO_4$, $Li_{(2-j)}Fe_kNi_lSiO_4$, $Li_{(2-j)}Fe_kCo_lSiO_4$, $Li_{(2-j)}Fe_kMn_lSiO_4$, $Li_{(2-j)}Ni_kCo_lSiO_4$, $Li_{(2-j)}Ni_kMn_lSiO_4$ (k+l≤1, 0<k<1, and 0<l<1), $Li_{(2-j)}Fe_mNi_nCo_qSiO_4$, $Li_{(2-j)}Fe_mNi_nMn_qSiO_4$, $Li_{(2-j)}Ni_mCo_nMn_qSiO_4$ (m+n+q≤1, 0<m<1, 0<n<1, and 0<q<1), and $Li_{(2-j)}Fe_rNi_sCo_tMn_uSiO_4$ (r+s+t+u≤1, 0<r<1, 0<s<1, 0<t<1, and 0<u<1).

Still alternatively, a NASICON compound represented by $A_xM_2(XO_4)_3$ in a general formula (A=Li, Na, or Mg; M=Fe, Mn, Ti, V, Nb, or Al; X=S, P, Mo, W, As, or Si; 0≤x≤5) can be used as the positive electrode active material. Examples of the NASICON compound are $Fe_2(MnO_4)_3$, $Fe_2(SO_4)_3$, and $Li_3Fe_2(PO_4)_3$. Further alternatively, for example, a compound represented by $Li_2MPO_4F$, $Li_2MP_2O_7$, or $Li_5MO_4$ (general formula) (M=Fe or Mn), a perovskite fluoride such as $NaFeF_3$ and $FeF_3$, a metal chalcogenide (a sulfide, a selenide, or a telluride) such as $TiS_2$ and $MoS_2$, a lithium-containing material with an inverse spinel structure such as $LiMVO_4$, vanadium oxide ($V_2O_5$, $V_6O_{13}$, $LiV_3O_8$, or the like), manganese oxide, or an organic sulfur compound can be used as the positive electrode active material.

In the case where carrier ions are alkali metal ions other than lithium ions or alkaline-earth metal ions, the following may be used as the positive electrode active material: a compound or an oxide which is obtained by substituting an alkali metal (e.g., sodium or potassium) or an alkaline-earth metal (e.g., calcium, strontium, barium, beryllium, or magnesium) for lithium in any of the aforementioned compounds or oxides. For example, the positive electrode active material may be a layered oxide containing sodium such as $NaFeO_2$ or $Na_{2/3}[Fe_{1/2}Mn_{1/2}]O_2$.

Further alternatively, any of the aforementioned materials may be combined to be used as the positive electrode active material. For example, a solid solution obtained by combining two or more of the aforementioned materials can be used as the positive electrode active material. For example, a solid solution of $LiCo_{1/3}Mn_{1/3}Ni_{1/3}O_2$ and $Li_2MnO_3$ can be used as the positive electrode active material.

The average particle diameter of primary particles of the positive electrode active material is preferably greater than or equal to 50 nm and less than or equal to 100 μm.

The positive electrode active material and a negative electrode active material have a main role in battery reactions of the power storage device, and receive and release carrier ions. To increase the lifetime of the power storage device, a material that has a small amount of capacity relating to irreversible battery reactions and has high charge and discharge efficiency is preferably used for the active materials.

The active material is in contact with an electrolyte. When the active material reacts with the electrolyte, the active material is lost and deteriorates by the reaction, which decreases the capacity of the power storage device. Therefore, it is preferable that such a reaction not be caused in the power storage device so that the power storage device hardly deteriorates.

Examples of the conductive additive of the electrode include acetylene black (AB), graphite (black lead) particles, carbon nanotubes, graphene, and fullerene.

A network for electronic conduction can be formed in the electrode by the conductive additive. The conductive additive also allows maintaining of a path for electronic conduction between the positive electrode active materials. The addition of the conductive additive to the positive electrode active material layer increases the electronic conductivity of the positive electrode active material layer 101.

A typical example of the binder is polyvinylidene fluoride (PVDF), and other examples of the binder include polyimide, polytetrafluoroethylene, polyvinyl chloride, ethylene-propylene-diene polymer, fluorine rubber, polymethyl methacrylate, polyethylene, and nitrocellulose.

The content of the binder in the positive electrode active material layer 101 is preferably greater than or equal to 0.5 wt % and less than or equal to 10 wt %, further preferably greater than or equal to 2 wt % and less than or equal to 8 wt %, and still further preferably greater than or equal to 3 wt % and less than or equal to 5 wt %. The content of the conductive additive in the positive electrode active material layer 101 is preferably greater than or equal to 1 wt % and less than or equal to 10 wt %, further preferably greater than or equal to 1 wt % and less than or equal to 5 wt %.

In the case where the positive electrode active material layer 101 is formed by a coating method, the positive electrode active material, the binder, the conductive additive, and a dispersion medium are mixed to form an electrode slurry, and the electrode slurry is applied to the positive electrode current collector 100 and dried.

The positive electrode active material layer 101 may be formed into a thin film by a sputtering method or the like.

The positive electrode current collector 100 can be formed using a material which has high electronic conductivity such as stainless steel, gold, platinum, aluminum, or titanium, or an alloy thereof. Alternatively, an aluminum alloy to which an element which improves heat resistance, such as silicon, titanium, neodymium, scandium, or molybdenum, is added can be used. A part of the surface of the positive electrode current collector may be provided with an undercoat layer using graphite or the like. The positive electrode current collector 100 can have a foil-like shape, a plate-like shape (sheet-like shape), a net-like shape, a cylindrical shape, a coil shape, a punching-metal shape, an expanded-metal shape, or the like as appropriate.

Through the above steps, the positive electrode of the lithium-ion storage battery can be formed.

<<Structure of Negative Electrode>>

Next, the negative electrode is described. The negative electrode includes the negative electrode active material layer 103 and the negative electrode current collector 102. Steps of forming the negative electrode are described below.

Examples of a carbon-based material as the negative electrode active material used for the negative electrode active material layer 103 include graphite, graphitizing carbon (soft carbon), non-graphitizing carbon (hard carbon), a carbon nanotube, graphene, and carbon black. Examples of graphite include artificial graphite such as meso-carbon microbeads (MCMB), coke-based artificial graphite, or pitch-based artificial graphite and natural graphite such as spherical natural graphite. In addition, examples of the shape of graphite include a flaky shape and a spherical shape.

Other than the carbon-based material, a material that enables charge-discharge reactions by an alloying reaction and a dealloying reaction with lithium can be used as the negative electrode active material. For example, a material containing at least one of Ga, Si, Al, Ge, Sn, Pb, Sb, Bi, Ag, Zn, Cd, In, and the like can be used. Such elements have a higher capacity than carbon. In particular, silicon is preferably used because of its high theoretical capacity of 4200 mAh/g. Examples of the alloy-based material containing such elements include $Mg_2Si$, $Mg_2Ge$, $Mg_2Sn$, $SnS_2$, $V_2Sn_3$, $FeSn_2$, $CoSn_2$, $Ni_3Sn_2$, $Cu_6Sn_5$, $Ag_3Sn$, $Ag_3Sb$, $Ni_2MnSb$, $CeSb_3$, $LaSn_3$, $La_3Co_2Sn_7$, $CoSb_3$, $InSb$, and $SbSn$.

Alternatively, for the negative electrode active material, an oxide such as $SiO$, $SnO$, $SnO_2$, titanium dioxide ($TiO_2$), lithium titanium oxide ($Li_4Ti_5O_{12}$), lithium-graphite intercalation compound ($Li_xC_6$), niobium pentoxide ($Nb_2O_5$), tungsten oxide ($WO_2$), or molybdenum oxide ($MoO_2$) can be used.

Still alternatively, for the negative electrode active material, $Li_{(3-x)}M_xN$ (M is Co, Ni, or Cu) with a $Li_3N$ structure, which is a nitride containing lithium and a transition metal, can be used. For example, $Li_{2.6}Co_{0.4}N_3$ is preferable because of its high charge and discharge capacity (900 mAh/g and 1890 mAh/cm$^3$).

When a nitride containing lithium and a transition metal is used, lithium is contained in the negative electrode active material and thus the negative electrode active material can be used in combination with a material for a positive electrode active material that does not contain lithium, such as $V_2O_5$ or $Cr_3O_8$. In the case of using a material containing lithium as a positive electrode active material, the nitride containing lithium and a transition metal can be used for the negative electrode active material by extracting lithium contained in the positive electrode active material in advance.

Alternatively, a material which causes a conversion reaction can be used as the negative electrode active material. For example, a transition metal oxide with which an alloying reaction with lithium is not caused, such as cobalt oxide (CoO), nickel oxide (NiO), or iron oxide (FeO), may be used for the negative electrode active material. Other examples of the material which causes a conversion reaction include oxides such as $Fe_2O_3$, CuO, $Cu_2O$, $RuO_2$, and $Cr_2O_3$, sulfides such as $CoS_{0.89}$, NiS, and CuS, nitrides such as $Zn_3N_2$, $Cu_3N$, and $Ge_3N_4$, phosphides such as $NiP_2$, $FeP_2$, and $CoP_3$, and fluorides such as $FeF_3$ and $BiF_3$.

The particle diameter of the negative electrode active material is preferably greater than or equal to 50 nm and less than or equal to 100 μm, for example.

Note that a plurality of materials for active materials can be combined at a given proportion both for the positive electrode active material layer 101 and the negative electrode active material layer 103. The use of a plurality of materials for the active material layer makes it possible to select the property of the active material layer in more detail.

Examples of the conductive additive in the electrode include acetylene black (AB), graphite (black lead) particles, carbon nanotubes, graphene, and fullerene.

A network for electronic conduction can be formed in the electrode by the conductive additive. The conductive additive also allows maintaining of a path for electronic conduction between the negative electrode active materials. The addition of the conductive additive to the negative electrode active material layer increases the electronic conductivity of the negative electrode active material layer 103.

A typical example of the binder is polyvinylidene fluoride (PVDF), and other examples of the binder include polyimide, polyvinyl chloride, ethylene-propylene-diene polymer, styrene-butadiene rubber, sodium carboxymethyl cellulose, acrylonitrile-butadiene rubber, fluorine rubber, polyvinyl acetate, polymethyl methacrylate, polyethylene, and nitrocellulose.

The content of the binder in the negative electrode active material layer 103 is preferably greater than or equal to 1 wt % and less than or equal to 10 wt %, further preferably greater than or equal to 2 wt % and less than or equal to 8 wt %, and still further preferably greater than or equal to 3 wt % and less than or equal to 5 wt %. The content of the conductive additive in the negative electrode active material layer 103 is preferably greater than or equal to 1 wt % and less than or equal to 10 wt %, further preferably greater than or equal to 1 wt % and less than or equal to 5 wt %.

Next, the negative electrode active material layer 103 is formed over the negative electrode current collector 102. In the case where the negative electrode active material layer 103 is formed by a coating method, the negative electrode active material, the binder, the conductive additive, and a dispersion medium are mixed to form a slurry, and the slurry is applied to the negative electrode current collector 102 and dried. If necessary, pressing may be performed after the drying.

The negative electrode active material layer 103 may be formed into a thin film by a sputtering method or the like.

The negative electrode current collector 102 can be formed using a material which has high electronic conductivity and is not alloyed with a carrier ion of lithium or the like, such as stainless steel, gold, platinum, iron, copper, titanium, or tantalum, or an alloy thereof. Alternatively, a metal element which forms silicide by reacting with silicon can be used. Examples of the metal element which forms silicide by reacting with silicon include zirconium, titanium, hafnium, vanadium, niobium, tantalum, chromium, molybdenum, tungsten, cobalt, and nickel. The negative electrode current collector 102 can have a foil-like shape, a plate-like shape (sheet-like shape), a net-like shape, a cylindrical shape, a coil shape, a punching-metal shape, an expanded-metal shape, or the like as appropriate. The negative electrode current collector 102 preferably has a thickness greater than or equal to 5 μm and less than or equal to 30 μm. Part of the surface of the negative electrode current collector may be provided with an undercoat layer using graphite or the like. In the case where a high-potential material such as lithium titanium oxide ($Li_4Ti_5O_{12}$) is used for the negative electrode active material, aluminum can be used for the negative electrode current collector 102.

Through the above steps, the negative electrode of the lithium-ion storage battery can be formed.

<<Structure of Solid Electrolyte Layer>>

In the case of using the graphene compound of one embodiment of the present invention for a solid electrolyte layer, the graphene compound may be mixed with a lithium salt.

For example, a dispersion liquid obtained by dispersing the graphene compound of one embodiment of the present invention in tetrahydrofuran (THF) and a solution obtained by dispersing a lithium salt in THF are mixed. Next, one or several drops of the mixed solution are dripped into a material of a solid electrolyte layer, the material is simply dried using a hot plate, and then drying is performed at 90° C. under reduced pressure to form the solid electrolyte layer. The solid electrolyte layer is in a film form in some cases. The solid electrolyte layer is provided between the positive electrode and the negative electrode and stored in the exterior body.

The graphene compound of one embodiment of the present invention has high dispersibility in a polar solvent because of having a functional group containing an ester bond or an amide group. Owing to the high dispersibility in a polar solvent, the solid electrolyte layer is easily formed into a film by the aforementioned method.

As the lithium salt, for example, one or more of $LiPF_6$, $LiClO_4$, $LiAsF_6$, $LiBF_4$, $LiAlCl_4$, LiSCN, LiBr, LiI, $Li_2SO_4$, $Li_2B_{10}Cl_{10}$, $Li_2B_{12}Cl_{12}$, $LiCF_3SO_3$, $LiC_4F_9SO_3$, $LiC(CF_3SO_2)_3$, $LiC(C_2F_5SO_2)_3$, $LiN(CF_3SO_2)_2$, $LiN(C_4F_9SO_2)$, $(CF_3SO_2)$, $LiN(C_2F_5SO_2)_2$, and the like can be used.

Note that a method for mixing the lithium salt with the graphene compound, which is employed in the case of using the graphene compound of one embodiment of the present invention for a solid electrolyte layer, is not limited thereto.

Alternatively, a mixture of the graphene compound to which the lithium salt is mixed and one or more of an oxide-based solid electrolyte, a sulfide-based solid electrolyte, and a polymer electrolyte may be used as the solid electrolyte layer.

As the oxide-based solid electrolyte, for example, one or more of $La_{0.51}Li_{0.34}TiO_{2.94}$, $Li_{1.3}Al_{0.3}Ti_{1.7}(PO_4)_3$, $Li_7La_3Zr_2O_{12}$, $50Li_4SiO_4 \cdot 50Li_3BO_3$, $Li_{2.9}PO_{3.3}N_{0.46}$, $Li_{3.6}Si_{0.6}P_{0.4}O_4$, $Li_{1.07}Al_{0.69}Ti_{1.46}(PO_4)_3$, $Li_{1.5}Al_{0.5}Ge_{1.5}(PO_4)_3$, and the like can be used.

As the sulfide-based solid electrolyte, for example, one or more of $Li_{10}GeP_2S_{12}$, $Li_{3.25}Ge_{0.25}P_{0.75}S_4$, $30Li_2S \cdot 26B_2S_3 \cdot 44LiI$, $63Li_2S \cdot 36SiS_2 \cdot Li_3PO_4$, $57Li_2S \cdot 38SiS_2 \cdot 5Li_4SiO_4$, $70Li_2S \cdot 30P_2S_5$, $50Li_2S \cdot 50GeS_2$, $Li_7P_3S_{11}$, $Li_{3.25}P_{0.95}S_4$, and the like can be used.

As the polymer electrolyte, for example, one or more of polyethylene oxide, polypropylene oxide, polyethyleneimine, and the like can be used. The polymer electrolyte in which a lithium salt is dissolved can also be used.

The solid electrolyte layer may include a plurality of layers. That is, a first solid electrolyte layer and a second solid electrolyte layer which are formed by different methods can be used together in the power storage device. The first solid electrolyte layer and the second solid electrolyte layer may be formed by the same method.

The power storage device may be flexible. Since a graphene compound has flexibility, the solid electrolyte layer including a graphene compound can have flexibility.

<<Structure of Separator>>

A separator is described. The separator needs to have ionic conductivity and an insulation property that prevents connection between the electrodes.

A solid electrolyte layer of a solid-state battery may also function as a separator. As a material for the separator, a graphene compound of one embodiment of the present invention that is to be the solid electrolyte layer can be used (see FIGS. 1A and 1B).

In addition to the solid electrolyte layer using the graphene compound, a separator may also be provided. As a material for the separator, high-molecular compounds based on fluorine-based polymer, polyether such as polyethylene oxide and polypropylene oxide, polyolefin such as polyethylene and polypropylene, polyacrylonitrile, polyvinylidene chloride, polymethyl methacrylate, polymethylacrylate, polyvinyl alcohol, polymethacrylonitrile, polyvinyl acetate, polyvinylpyrrolidone, polyethyleneimine, polybutadiene, polystyrene, polyisoprene, and polyurethane, derivatives thereof, cellulose, paper, nonwoven fabric, and a glass fiber can be used either alone or in combination. By using two separators having different characteristics in combination, the performance of the separators of the power storage device can be selected more variously than in the case of using one of the separators.

To incorporate the solid electrolyte layer and the separator in the power storage device, a method in which the solid electrolyte layer and the separator are inserted between the positive electrode and the negative electrode can be used. Alternatively, after the solid electrolyte layer and the separator are placed on one of the positive electrode and the negative electrode, the other of the positive electrode and the negative electrode can be stacked thereon. The positive electrode, the negative electrode, the solid electrolyte layer, and the separator are stored in the exterior body, whereby the power storage device can be fabricated.

Figure 2:
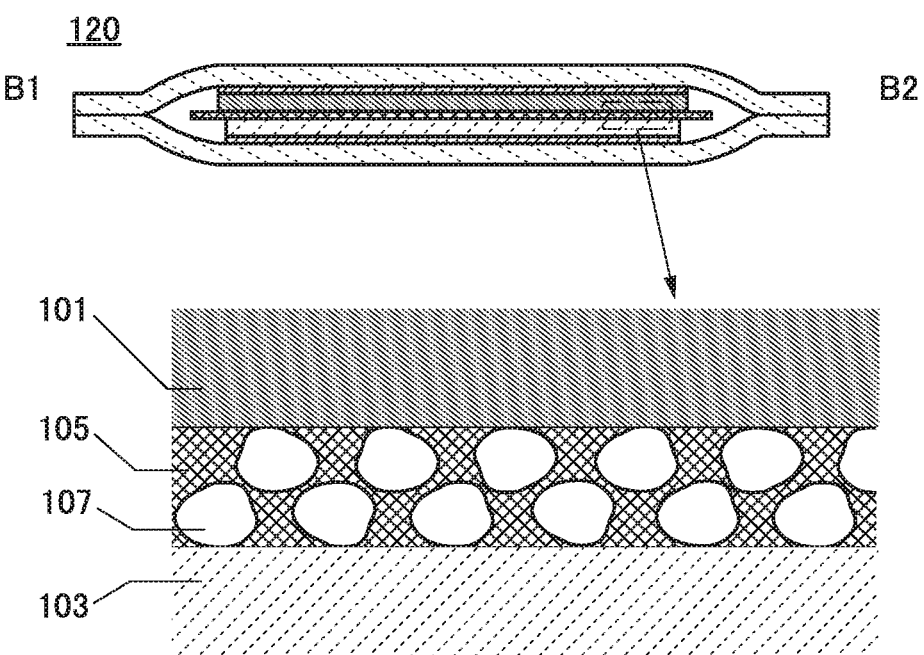
FIG. 2 illustrates a lithium-ion storage battery.

A schematic view of a lithium-ion storage battery 120 including a solid electrolyte layer and separators is illustrated in FIG. 2. FIG. 2 is an enlarged view of the positive electrode active material layer 101, the negative electrode active material layer 103, a graphene compound 105 that is a solid electrolyte layer, and separators 107. The graphene compound 105 that is a solid electrolyte layer and the separators 107 are provided between the positive electrode active material layer 101 and the negative electrode active material layer 103. The graphene compound 105 that is a solid electrolyte layer fills gaps between fibers of the separators 107 and is in contact with the positive electrode active material layer 101 and the negative electrode active material layer 103. Such a structure is preferable because a short circuit between the positive electrode and the negative electrode is prevented more effectively. Although the separator having a fiber-like shape is described as an example, the shape of the separator is not limited thereto.

The solid electrolyte layer and the separator with a size large enough to cover each surface of either the positive electrode or the negative electrode, in a form of sheet or envelope, may be fabricated to form the electrode wrapped in the solid electrolyte layer and the separator. In that case, the electrode can be protected from mechanical damages in the fabrication of the power storage device, which facilitates the handling of the electrode. The electrode wrapped in the separator and the other electrode are provided in the exterior body, whereby the power storage device can be fabricated.

The separator 107 and the graphene compound 105 may each include a plurality of layers. For example, a first separator 107, a graphene compound 105 that is a first solid electrolyte layer, a second separator 107, and a graphene compound 105 that is a second solid electrolyte layer may be stacked in this order. Also in the case of using the plurality of layers, the graphene compound 105 that is a solid electrolyte layer may fill gaps between fibers of the separators 107 and may be in contact with the positive electrode active material layer 101 and the negative electrode active material layer 103.

Furthermore, the power storage device may be flexible. In the case where flow stress is applied to the flexible power storage device, the stress can be relieved because the first separator and the second separator slide at the interface therebetween. Therefore, the structure including a plurality of separators is also suitable as a structure of the separator in the flexible power storage device.

Through the above steps, the separator can be incorporated in the lithium-ion storage battery.

<<Structure of Exterior Body>>

Next, the exterior body 109 is described. As the exterior body 109, a film having a three-layer structure formed as follows can be used; for example, a highly flexible metal thin film of aluminum, stainless steel, copper, nickel, or the like is provided over a film formed of a material such as polyethylene, polypropylene, polycarbonate, ionomer, or polyamide, and an insulating synthetic resin film of a polyamide-based resin, a polyester-based resin, or the like is provided as the outer surface of the exterior body over the metal thin film. With such a three-layer structure, permeation of the electrolyte and a gas can be blocked and an insulating property and resistance to the electrolyte can be obtained. The resistance to the electrolyte means corrosion resistance to the electrolyte. The exterior body is folded inwardly with one portion overlapping with another portion thereof, or two exterior bodies are stacked with the inner surfaces facing each other, in which case application of heat melts the materials on the overlapping inner surfaces to cause fusion bonding between the two exterior bodies. In this manner, a sealing structure can be formed.

A portion where the sealing structure is formed by fusion bonding or the like of the exterior body is referred to as a sealing portion. In the case where the exterior body is folded inwardly, the sealing portion is formed in the place other than the fold, and a first region of the exterior body and a second region of the exterior body that overlaps with the first region are fusion-bonded, for example. In the case where two exterior bodies are stacked, the sealing portion is formed along the entire outer region by heat fusion bonding or the like.

<<Flexible Power Storage Device>>

With use of a flexible material selected from materials of the members described in this embodiment, a flexible lithium-ion storage battery can be fabricated. Deformable devices are currently under active research and development. For such devices, flexible power storage devices are demanded.

In the case of bending a power storage device in which a battery material 1805 including electrodes, an electrolyte, and the like is sandwiched between two films as exterior bodies, a radius 1802 of curvature of a film 1801 close to a center 1800 of curvature of the power storage device is smaller than a radius 1804 of curvature of a film 1803 far from the center 1800 of curvature (FIG. 3A). When the power storage device is curved and has an arc-shaped cross section, compressive stress is applied to a surface of the film on the side closer to the center 1800 of curvature and tensile stress is applied to a surface of the film on the side farther from the center 1800 of curvature (FIG. 3B).

When the flexible lithium-ion storage battery is deformed, a high stress is applied to the exterior bodies. However, even with the compressive stress and tensile stress due to the deformation of the power storage device, the influence of a strain can be reduced by forming a pattern including projections or depressions on surfaces of the exterior bodies. For this reason, the power storage device can change its shape such that the exterior body on the side closer to the center of curvature has a curvature radius of 50 mm, preferably 30 mm.

Figure 4A:
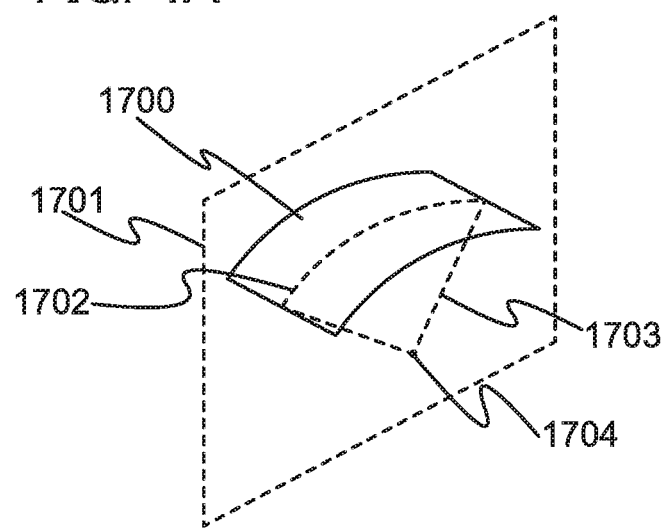
FIGS. 4A to 4C illustrate a flexible lithium-ion storage battery.
Figure 4B:
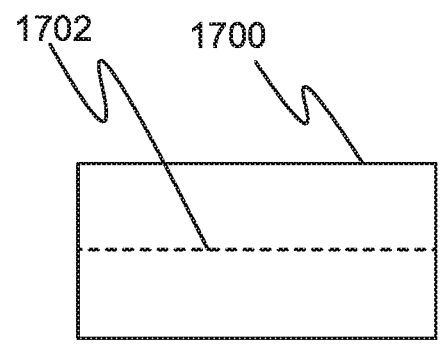
Figure 4C:
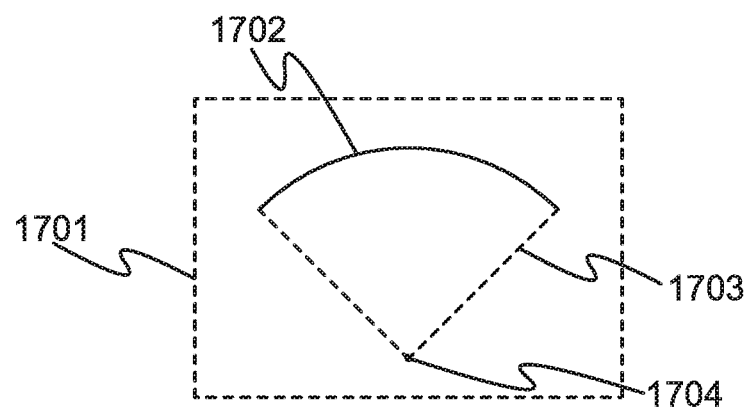

The radius of curvature of a surface is described with reference to FIGS. 4A to 4C. In FIG. 4A, on a plane 1701 along which a curved surface 1700 is cut, part of a curve 1702 forming the curved surface 1700 is approximate to an arc of a circle; the radius of the circle is referred to as a radius of curvature 1703 and the center of the circle is referred to as a center 1704 of curvature. FIG. 4B is a top view of the curved surface 1700. FIG. 4C is a cross-sectional view of the curved surface 1700 taken along the plane 1701. When a curved surface is cut along a plane, the radius of curvature of a curve in a cross section differs depending on the angle between the curved surface and the plane or on the cut position, and the smallest radius of curvature is defined as the radius of curvature of a surface in this specification and the like.

Note that the cross-sectional shape of the power storage device is not limited to a simple arc shape, and the cross section can be partly arc-shaped; for example, a shape illustrated in FIG. 3C, a wavy shape illustrated in FIG. 3D, or an S shape can be used. When the curved surface of the power storage device has a shape with a plurality of centers of curvature, the power storage device can change its shape such that a curved surface with the smallest radius of curvature among radii of curvature with respect to the plurality of centers of curvature, which is a surface of the exterior body on the side closer to the center of curvature, has a curvature radius of 50 mm, preferably 30 mm.

<<Assembly of Power Storage Device and Aging>>

Next, the above-mentioned components are combined and enclosed in the exterior body 109, so that the positive electrode current collector 100, the positive electrode active material layer 101, the graphene compound 105 that is a solid electrolyte layer, the negative electrode active material layer 103, and the negative electrode current collector 102 are stacked and enclosed in the exterior body 109 as illustrated in FIGS. 1A and 1B.

Then, an aging step may be performed. First, the environmental temperature is kept at about room temperature for example, and constant current charge is performed to a predetermined voltage at a low rate. In the case where the charge generates a gas inside the exterior body, the generated gas is released outside the exterior body, and then charge is performed at a higher rate than the initial charge.

After that, the power storage battery is preserved at relatively high temperatures for a long time. For example, the power storage battery is kept at higher than or equal to 40° C. for longer than or equal to 24 hours.

After the long-time preservation at relatively high temperatures, a gas, if generated inside the exterior body, is released outside. Furthermore, the power storage device is discharged at room temperature, charged at the same rate, discharged at the same rate again, and further charged at the same rate. Then, discharge is performed at the same rate, which terminates the aging step.

In the aforementioned manner, the power storage device of one embodiment of the present invention can be fabricated.

This embodiment can be combined with any of the other embodiments as appropriate.

Note that in the case where at least one specific example is described in a diagram or text described in one embodiment in this specification and the like, it will be readily appreciated by those skilled in the art that a broader concept of the specific example can be derived. Therefore, in the diagram or the text described in one embodiment, in the case where at least one specific example is described, a broader concept of the specific example is disclosed as one embodiment of the invention, and one embodiment of the invention can be constituted. The embodiment of the invention is clear.

Note that in this specification and the like, a content described in at least a diagram (which may be part of the diagram) is disclosed as one embodiment of the invention, and one embodiment of the invention can be constituted. Therefore, when a certain content is described in a diagram, the content is disclosed as one embodiment of the invention even when the content is not described with text, and one embodiment of the invention can be constituted. In a similar manner, part of a diagram, which is taken out from the diagram, is disclosed as one embodiment of the invention, and one embodiment of the invention can be constituted. The embodiment of the invention is clear.

Embodiment 4

Described in this embodiment will be examples of electronic devices including the power storage devices of one embodiment of the present invention.

FIGS. 5A to 5F illustrate examples of electronic devices each including a power storage device. Examples of electronic devices each including a power storage device include television devices (also referred to as televisions or television receivers), monitors of computers or the like, digital cameras, digital video cameras, digital photo frames, cellular phones (also referred to as mobile phones or mobile phone devices), portable game machines, portable information terminals, audio reproducing devices, and large game machines such as pachinko machines.

In addition, a power storage device can be incorporated along a curved inside/outside wall surface of a house or a building or a curved interior/exterior surface of a car.

Figure 5A:
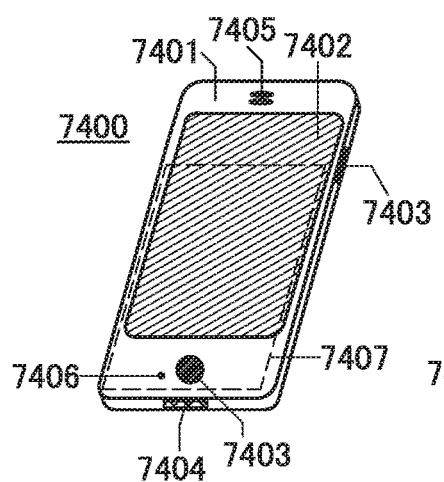
FIGS. 5A to 5F illustrate electronic devices of one embodiment of the present invention.

FIG. 5A illustrates an example of a cellular phone. A cellular phone 7400 includes a display portion 7402 incorporated in a housing 7401, operation buttons 7403, an external connection port 7404, a speaker 7405, a microphone 7406, and the like. Note that the cellular phone 7400 includes a power storage device 7407.

Figure 5B:
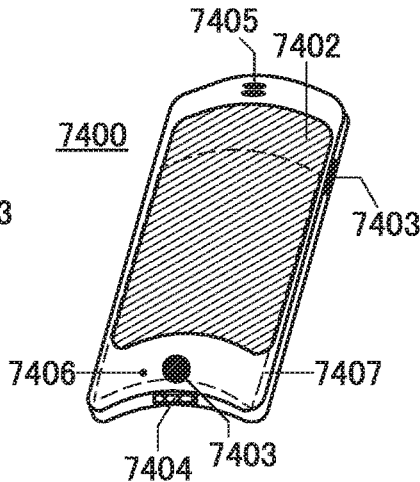
Figure 5C:
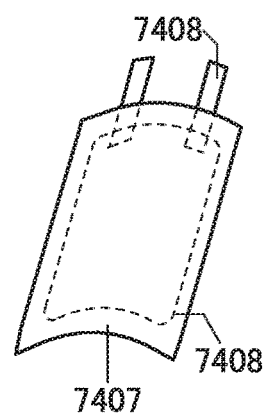

FIG. 5B illustrates the cellular phone 7400 that is bent. When the whole cellular phone 7400 is bent by external force, the power storage device 7407 included in the cellular phone 7400 is also bent. FIG. 5C illustrates the bent power storage device 7407. The power storage device 7407 is a thin power storage device. The power storage device 7407 is fixed while being bent. Note that the power storage device 7407 includes a lead electrode 7408 electrically connected to a current collector 7409.

Figure 5D:
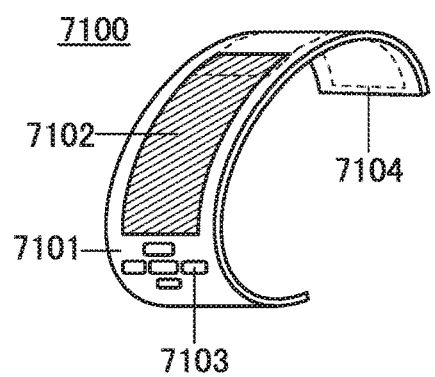
Figure 5E:
Figure 5F:
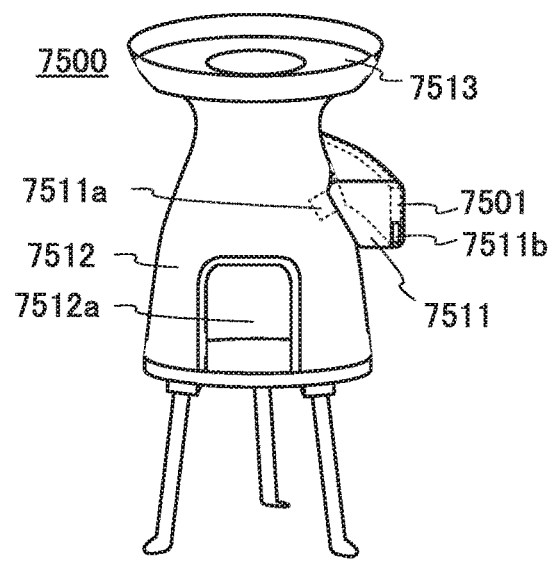

FIG. 5D illustrates an example of a bangle display device. A portable display device 7100 includes a housing 7101, a display portion 7102, operation buttons 7103, and a power storage device 7104. FIG. 5E illustrates the bent power storage device 7104. When the display device is worn on a user's arm while the power storage device 7104 is bent, the shape of the housing changes to change the curvature of part or the whole of the power storage device 7104. Note that the radius of curvature of a curve at a point refers to the radius of the circular arc that best approximates the curve at that point. The reciprocal of the radius of curvature is curvature. Specifically, part or the whole of the housing or the main surface of the power storage device 7104 is changed in the range of radius of curvature from 40 mm to 150 mm inclusive. When the radius of curvature at the main surface of the power storage device 7104 is 40 mm to 150 mm inclusive, the reliability can be kept high.

Furthermore, the flexile power storage device which can be bent by external force can be provided with high space efficiency in any of a variety of electronic devices. For example, in a stove 7500 illustrated in FIG. 5F, a module 7511 is attached to a main body 7512. The module 7511 includes a power storage device 7501, a motor, a fan, an air outlet 7511a, and a thermoelectric generation device. In the stove 7500, after a fuel is injected through an opening 7512a and ignited, outside air can be sent through the air outlet 7511a to the inside of the stove 7500 by rotating the motor and the fan which are included in the module 7511 using power of the power storage device 7501. In this manner, the stove 7500 can have strong heating power because outside air can be taken into the inside of the stove 7500 efficiently. In addition, cooking can be performed on an upper grill 7513 with thermal energy generated by the combustion of fuel. When the thermal energy is converted into power with the thermoelectric generation device of the module 7511, the power can be stored in the power storage device 7501. The power stored in the power storage device 7501 can be output through an external terminal 7511b.

Figure 6A:
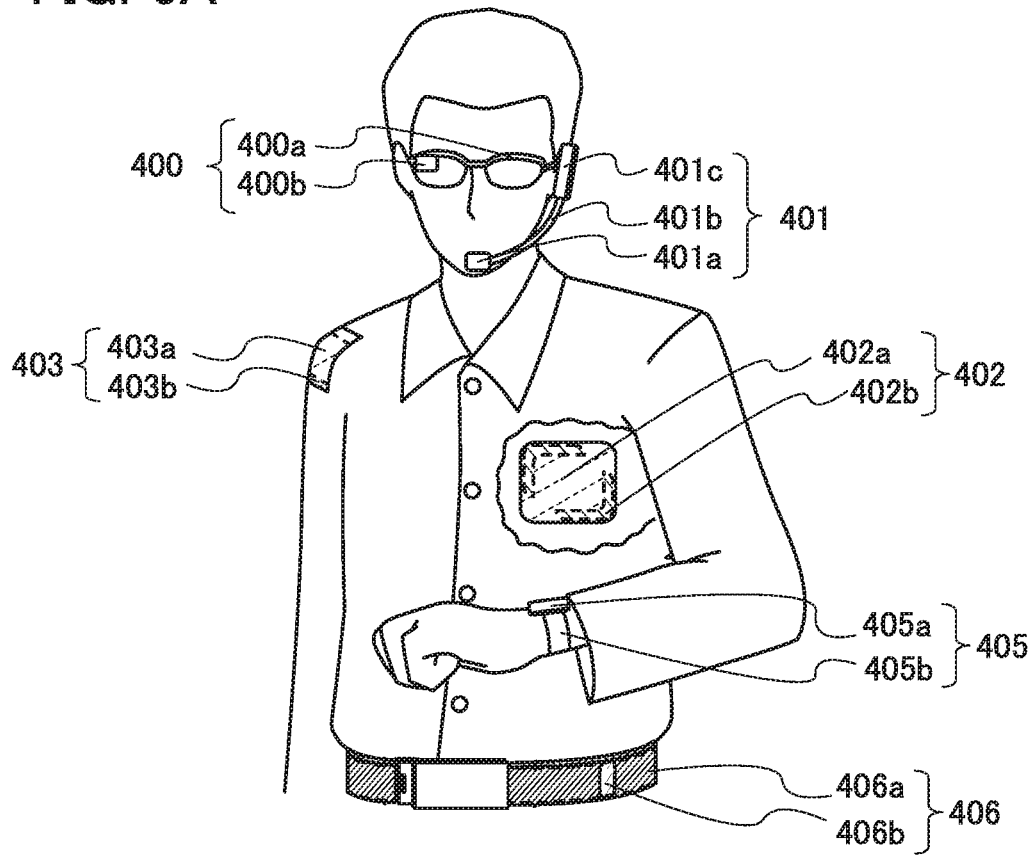
FIGS. 6A and 6B illustrate electronic devices of one embodiment of the present invention.

The power storage device using the graphene compound of one embodiment of the present invention can be provided in wearable devices illustrated in FIG. 6A.

For example, the power storage device can be provided in a glasses-type device 400 illustrated in FIG. 6A. The glasses-type device 400 includes a frame 400a and a display portion 400b. The power storage device is provided in a temple of the frame 400a having a curved shape, whereby the glasses-type device 400 can have a well-balanced weight and can be used continuously for a long time.

The power storage device can also be provided in a headset-type device 401. The headset-type device 401 includes at least a microphone portion 401a, a flexible pipe 401b, and an earphone portion 401c. The power storage device can be provided in the flexible pipe 401b and the earphone portion 401c.

Furthermore, the power storage device can be provided in a device 402 that can be attached directly to a body. A power storage device 402b can be provided in a thin housing 402a of the device 402.

Furthermore, the power storage device can be provided in a device 403 that can be attached to clothes. A power storage device 403b can be provided in a thin housing 403a of the device 403.

Furthermore, the power storage device can be provided in a watch-type device 405. The watch-type device 405 includes a display portion 405a and a belt portion 405b, and the power storage device can be provided in the display portion 405a or the belt portion 405b.

The display portion 405a can display various kinds of information such as time and reception information of an e-mail or an incoming call.

In addition, the watch-type device 405 is a wearable device that is wound around an arm directly; thus, a sensor that measures the pulse, the blood pressure, or the like of the user may be incorporated therein. Data on the exercise quantity and health of the user can be stored to be used for health maintenance.

Furthermore, the power storage device can be provided in a belt-type device 406. The belt-type device 406 includes a belt portion 406a and a wireless power feeding and receiving portion 406b, and the power storage device can be provided inside the belt portion 406a.

Figure 6B:
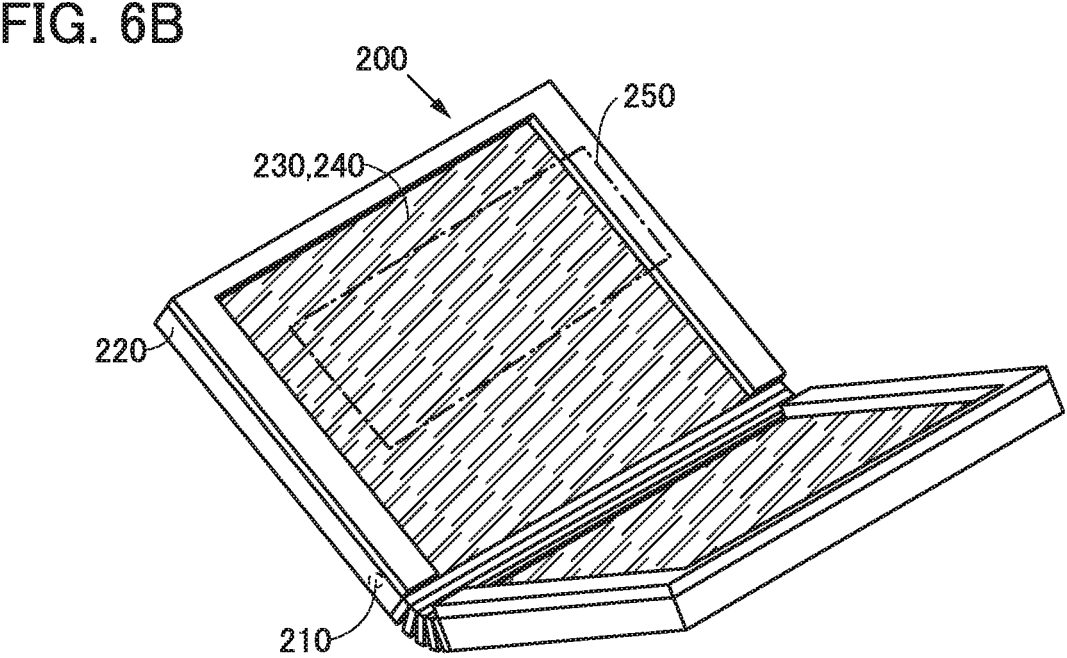

FIG. 6B is a projection view illustrating an example of an external view of a data processing device 200. The data processing device 200 described in this embodiment includes an arithmetic device 210, an input/output device 220, a display portion 230, and a power storage device 250.

The data processing device 200 includes a communication portion having a function of supplying data to a network and acquiring data from the network.

Furthermore, image data may be generated in accordance with received data delivered to a specific space using the communication portion. For example, educational materials distributed from a classroom of a school or a university can be received and displayed to be used as a schoolbook. Alternatively, materials distributed from a conference room in, for example, a company can be received and displayed.

This embodiment can be combined with any of the other embodiments as appropriate.

Embodiment 5

Described in this embodiment will be examples of a vehicle including the power storage device of one embodiment of the present invention.

The use of the power storage device in vehicles can lead to next-generation clean energy vehicles such as hybrid electric vehicles (HEVs), electric vehicles (EVs), and plug-in hybrid electric vehicles (PHEVs).

Figure 7A:
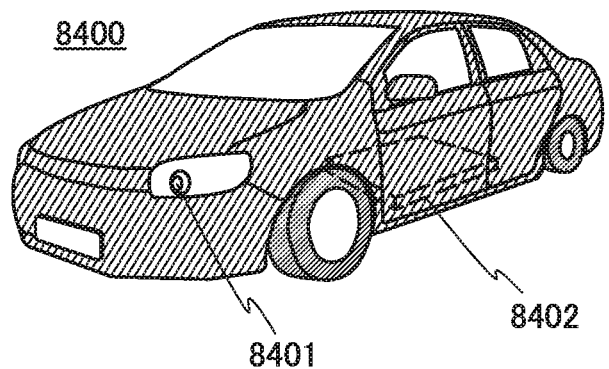
FIGS. 7A and 7B illustrate electronic devices of one embodiment of the present invention.

An automobile 8400 illustrated in FIG. 7A is an example of a hybrid electric vehicle (HEV) provided with a power storage device 8402. The power storage device 8402 is used as a power supply for driving a vehicle or a power supply of a headlight 8401 or the like.

Figure 7B:
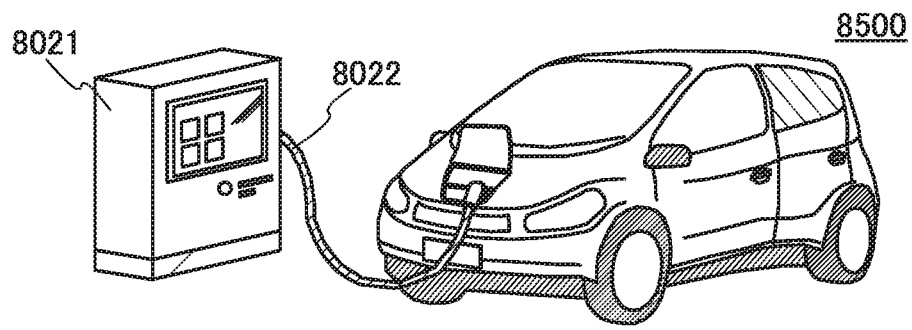

FIG. 7B illustrates an automobile 8500, which is an EV including the power storage device. The automobile 8500 can be charged when the power storage device is supplied with electric power through external charging equipment by a plug-in system, a contactless power feeding system, or the like. In FIG. 7B, a power storage device included in the automobile 8500 is charged with the use of a ground-based charging apparatus 8021 through a cable 8022. In charge, a given method such as CHAdeMO (registered trademark) or Combined Charging System may be employed as a charging method, the standard of a connector, or the like as appropriate. The charging apparatus 8021 may be a charging station provided in a commerce facility or a power source in a house. For example, with the use of a plug-in technique, the power storage device included in the automobile 8500 can be charged by being supplied with electric power from outside. The charge can be performed by converting AC electric power into DC electric power through a converter such as an AC-DC converter.

Furthermore, although not illustrated, the vehicle may include a power receiving device so as to be charged by being supplied with electric power from an above-ground power transmitting device in a contactless manner. In the case of the contactless power feeding system, by fitting a power transmitting device in a road or an exterior wall, charge can be performed not only when the electric vehicle is stopped but also when driven. In addition, the contactless power feeding system may be utilized to perform transmission and reception of electric power between vehicles. Furthermore, a solar cell may be provided in the exterior of the automobile to charge the power storage device when the automobile stops or moves. To supply electric power in such a contactless manner, an electromagnetic induction method or a magnetic resonance method can be used.

Furthermore, the power storage device included in the vehicle can be used as a power source for supplying electric power to products other than the vehicle. In such a case, the use of a commercial power source can be avoided at peak time of electric power demand.

An example of a motorcycle using one embodiment of the present invention will be described with reference to FIG. 8.

Figure 8:
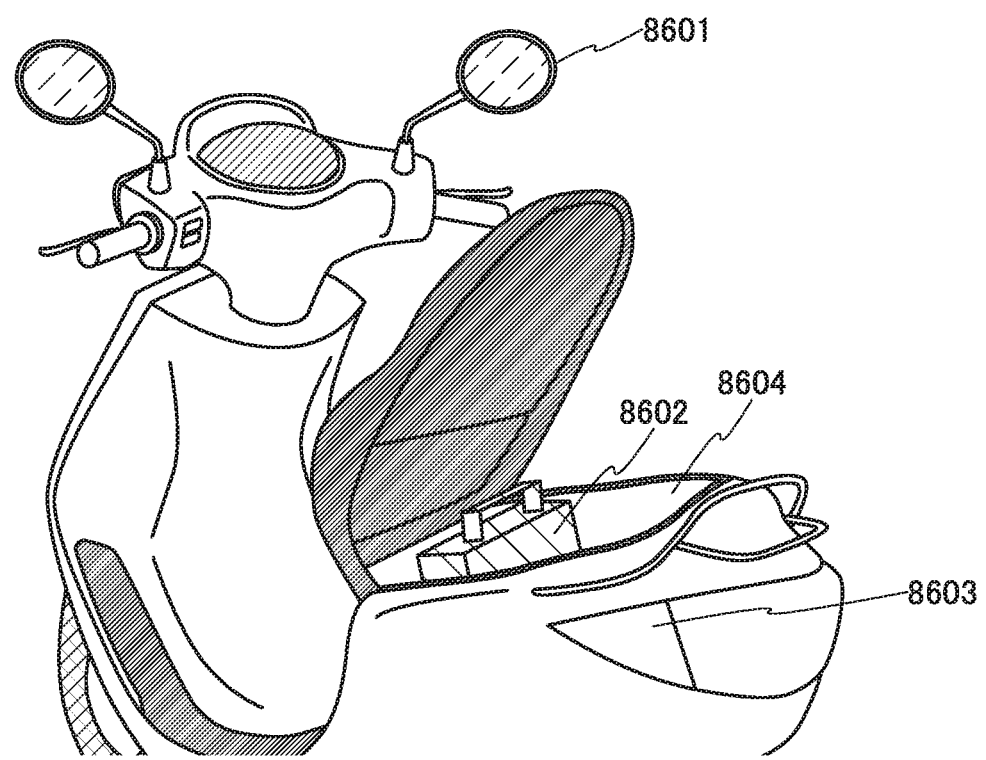
FIG. 8 illustrates an electronic device of one embodiment of the present invention.

A motor scooter 8600 illustrated in FIG. 8 includes a power storage device 8602, side mirrors 8601, and indicators 8603. The power storage device 8602 can supply electric power to the indicators 8603.

Furthermore, in the motor scooter 8600 illustrated in FIG. 8, the power storage device 8602 can be held in a storage unit under seat 8604. The power storage device 8602 can be held in the storage unit under seat 8604 even with a small size.

The power storage device 8602 used in this embodiment has high heat resistance and thus can be used in a severe environment, e.g., in a car for a long time. Furthermore, the power storage device 8602 in this embodiment can be used over a wide environmental temperature range and thus is useful.

This embodiment can be combined with any of the other embodiments as appropriate.

Example 1

In this example, synthesis examples of the graphene compound of one embodiment of the present invention described in Embodiment 1 are described.

Synthesis Example 1

A synthesis example of graphene oxide represented by a structural formula (501) shown below is described using synthesis schemes (T-12) to (T-14).

[Chemical formula 51]

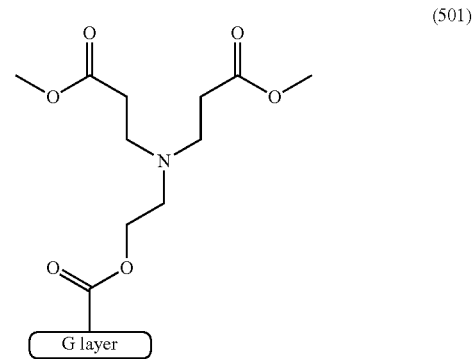

(501)

Into a flask were put 2-aminoethanol (2 g), methanol (50 ml), and methyl acrylate (6 g). This mixture was stirred at room temperature for 24 hours, and then, a solvent was removed. Thus, an objective pale yellow liquid substance represented by a structural formula (502) was obtained. This synthesis scheme (T-12) is shown below.

[Chemical formula 52]

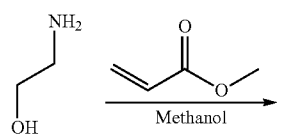

(T-12)

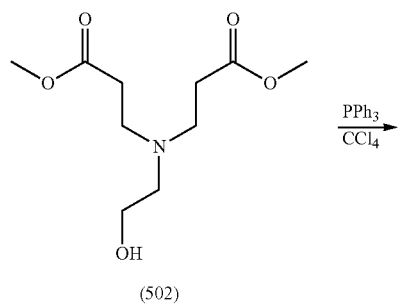

(502)

Into a flask were put the compound (3 g) represented by the structural formula (502), carbon tetrachloride (4.2 g), and triphenylphosphine (4.2 g). This mixture was stirred at 80° C. for three hours, and then, n-hexane (100 ml) was added thereto. After this mixture was filtered, a solid was removed, and then, a solvent was removed. Thus, an objective pale yellow liquid substance (2.3 g) represented by a structural formula (503) was obtained. The synthesis scheme (T-13) is shown below.

[Chemical formula 53]

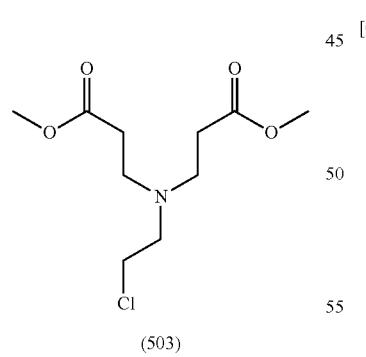

(T-13)

(502)

(503)

Into a flask were put graphene oxide (Rap dGO (TQ-11)-1 produced by NiSiNa materials Co., Ltd.) (395 mg) and N,N-dimethylformamide (DMF) (50 ml). Then, this flask was subjected to ultrasonic treatment for five minutes. Into this flask were put potassium carbonate (0.6 g) and the compound (2.3 g) represented by the structural formula (503). After this mixture was stirred at 60° C. for five hours, this mixture was washed with ethanol and water, and suction filtration was performed to collect a solid. A solvent contained in the obtained residue was removed. Thus, an objective black powder substance (294 mg) represented by the structural formula (501) was obtained. The synthesis scheme (T-14) is shown below.

[Chemical formula 54]

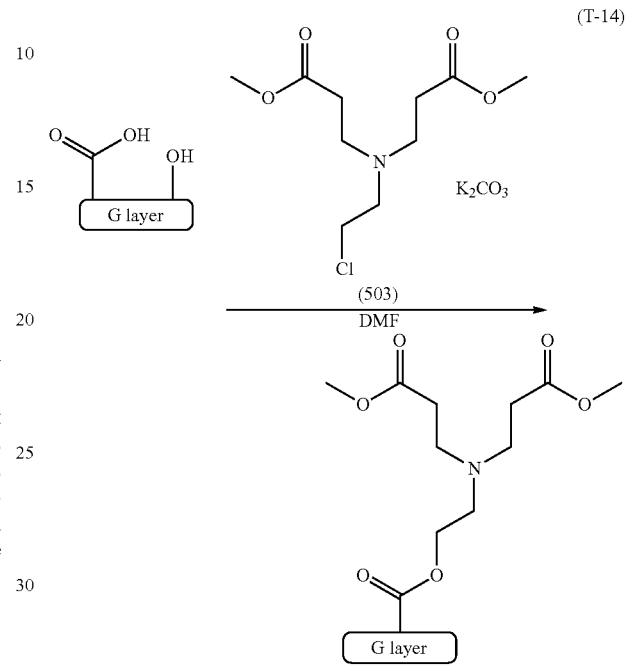

(T-14)

(501)

Synthesis Example 2

Then, a synthesis example of graphene oxide represented by a general formula (504) shown below is described using synthesis schemes (T-15) to (T-17).

[Chemical formula 55]

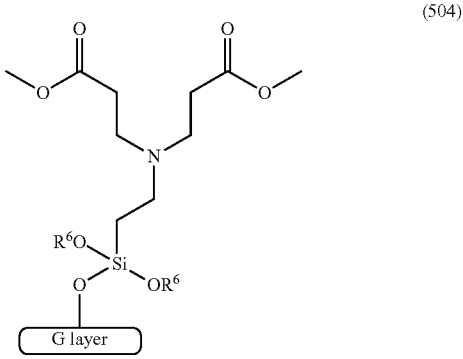

(504)

Note that in the general formula (504), $R^6$ represents a methyl group or a hydrogen atom.

Into a flask were put 3-aminopropyltrimethoxysilane (10 g) and methyl acrylate (10 g). This mixture was stirred at room temperature for 100 hours and then stirred at 50° C. for four hours. Methanol (20 ml) was added to this mixture, and the resulting mixture was stirred at 50° C. for four hours.

Then, a solvent contained in the mixture was removed. Thus, an objective colorless liquid substance (19 g) represented by a structural formula (505) was obtained. The synthesis scheme (T-15) is shown below.

[Chemical formula 56]

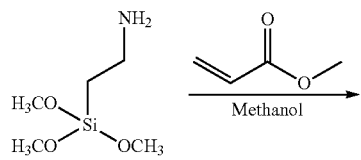

(T-15)

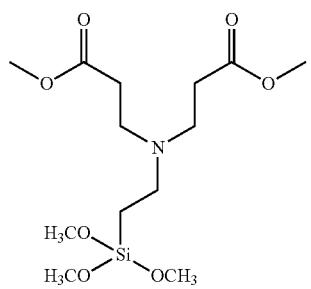

(505)

Into a flask were put the compound (19 g) represented by the structural formula (505), thionyl chloride (15 g), and DMF (1 g). This mixture was stirred in an ice bath for five minutes and then stirred in a nitrogen atmosphere at a temperature in a range from 50° C. to 60° C. for five hours. After diethyl ether and dichloromethane were added to the mixture, suction filtration was performed to remove a solid. Then, a solvent contained in this solution was removed. Thus, an objective brown liquid substance represented by a structural formula (506) was obtained. The synthesis scheme (T-16) is shown below.

[Chemical formula 57]

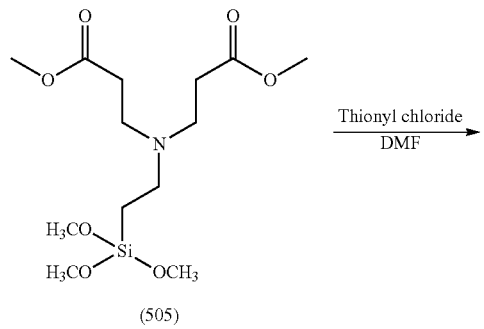

(T-16)

(505)

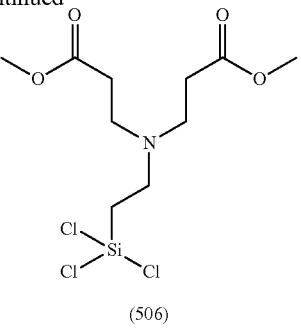

(506)

Into a flask were put a compound (400 mg) represented by the structural formula (506) and n-butylamine (5.6 g). Then, this flask was subjected to ultrasonic treatment for five minutes. The obtained mixture was stirred at 60° C. for one hour, and then, toluene (80 ml) was added to the mixture. This flask was subjected to ultrasonic treatment for five minutes. After this mixture was cooled to 0° C., a compound (12 g) represented by the structural formula (506) was added to this mixture, and then, the resulting mixture was stirred at 60° C. in a nitrogen atmosphere for five hours. This mixture was washed with toluene and ethanol, and suction filtration was performed to collect a solid. A solvent contained in the obtained residue was removed. Thus, an objective black powder substance (340 mg) represented by the structural formula (504) was obtained. The synthesis scheme (T-17) is shown below.

[Chemical formula 58]

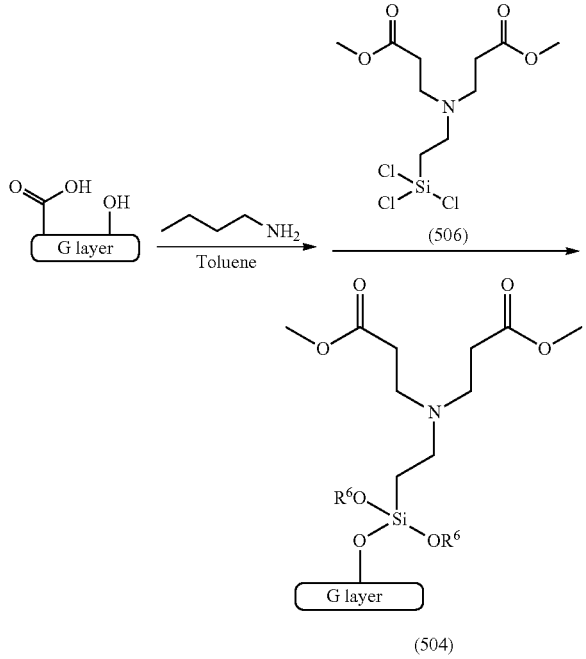

(504)

<FT-IR Analysis>

Fourier transform infrared spectroscopy (FT-IR) analysis was performed in order to confirm the chemical modification of the graphene compound in Synthesis example 1 and Synthesis example 2.

The chemically modified graphene compound (Sample 1) formed in Synthesis example 1, the chemically modified graphene compound (Sample 2) formed in Synthesis example 2, and chemically unmodified graphene oxide (Comparison sample 1) were subjected to FT-IR analysis.

In the FT-IR analysis, attenuated total reflection (ATR) was performed using Nicolet iS50 produced by Thermo Fisher Scientific Inc. The measurement range was from 400 $cm^{-1}$ to 4000 $cm^{-1}$, the resolution was 4.0 $cm^{-1}$, and the number of times of scanning was 16.

The sample was set to an analysis apparatus in a manner that the sample was pushed onto an ATR prism to bring the sample into close contact with the ATR prism.

Figure 9A:
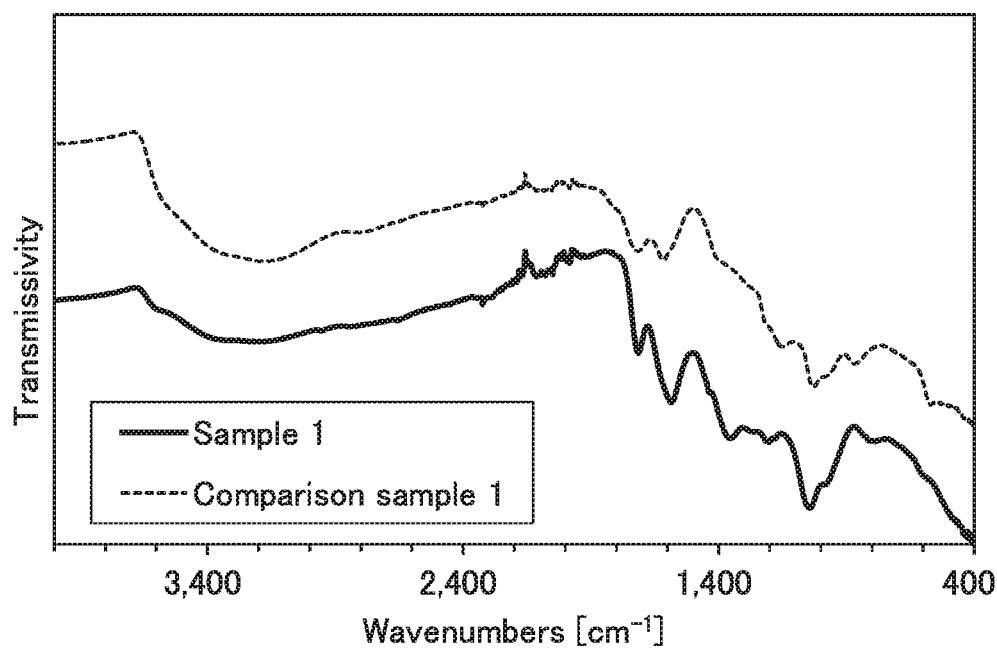
FIGS. 9A and 9B show results of FT-IR analyses.
Figure 9B:
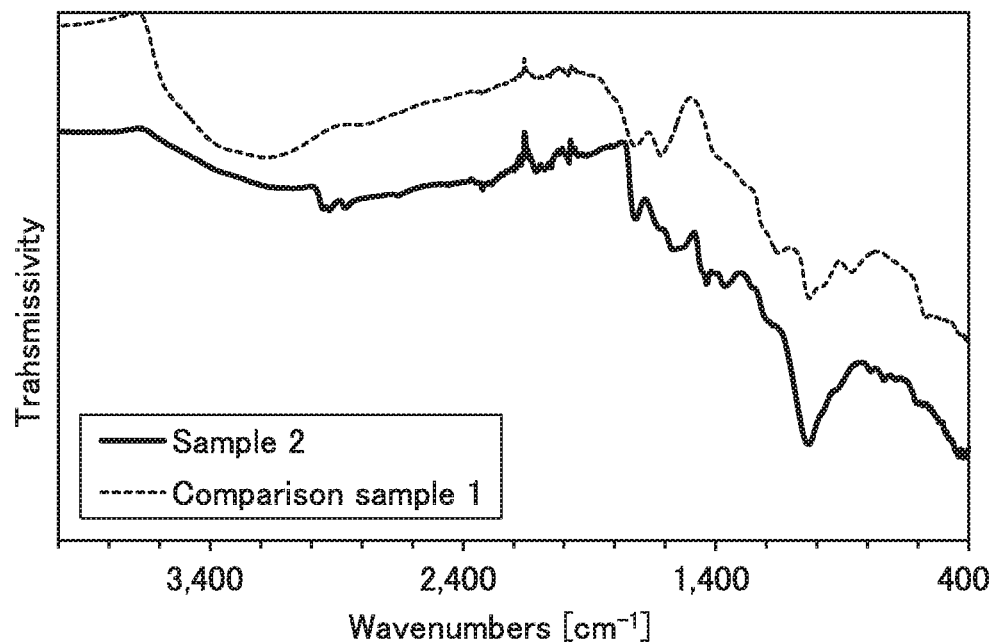

Results of the FT-IR analyses are shown in FIGS. 9A and 9B. FIG. 9A shows FT-IR spectra of Sample 1 and Comparison sample 1. FIG. 9B shows FT-IR spectra of Sample 2 and Comparison sample 1. The horizontal axis represents the wavenumber $[cm^{-1}]$ and the vertical axis represents the transmissivity [%] in each of FIGS. 9A and 9B.

Sample 1 and Comparison sample 1 were compared with each other in FIG. 9A. In the spectrum of Sample 1, broad absorption at around 3000 $cm^{-1}$ was decreased, and absorption in a range of 1000 $cm^{-1}$ to 1400 $cm^{-1}$ was increased.

The broad absorption at around 3000 $cm^{-1}$ is probably derived from O—H stretching vibration of carboxylic acid. Since the broad absorption at around 3000 $cm^{-1}$ is decreased, it is shown that carboxyl groups contained in Sample 1 are fewer than those contained in Comparison Sample 1. This may be because a carboxyl group contained in the graphene oxide corresponding to Sample 1 was chemically modified to form an ester bond.

The absorption in the range of 1000 $cm^{-1}$ to 1400 $cm^{-1}$ is probably derived from C—N stretching vibration, deformation vibration of a methyl group, deformation vibration of a methylene group, C—O stretching vibration of ester, or the like. Since the absorption in the range of 1000 $cm^{-1}$ to 1400 $cm^{-1}$ is increased, it is estimated that Sample 1 has a methyl group, a methylene group, a carbon-nitrogen bond, an ester bond, or the like.

Thus, it is confirmed that Sample 1 is chemically modified.

Sample 2 and Comparison sample 1 were compared with each other in FIG. 9B. In the spectrum of Sample 2, absorption at around 2900 $cm^{-1}$ is increased and broad absorption at around 3000 $cm^{-1}$ is decreased compared with Comparison sample 1.

The absorption at around 2900 $cm^{-1}$ is probably derived from C—H stretching vibration. Since the absorption at around 2900 $cm^{-1}$ is increased, it is shown that methyl groups contained in Sample 2 are greater in number than those contained in Comparison sample 1.

The broad absorption at around 3000 $cm^{-1}$ is probably derived from O—H stretching vibration of carboxylic acid. Since the broad absorption at around 3000 $cm^{-1}$ is decreased, it is shown that carboxyl groups contained in Sample 2 are fewer than those contained in Comparison Sample 1. This may be because a carboxyl group contained in the graphene oxide corresponding to Sample 2 was chemically modified to form an ester bond.

Thus, it is confirmed that Sample 2 is chemically modified.

<XRD Analysis>

XRD analysis was performed in order to determine the interlayer distance in the graphene compound synthesized in Synthesis example 2.

The XRD analysis was performed on the chemically modified graphene compound (Sample 2) formed in Synthesis example 2 and the chemically unmodified graphene oxide (Comparison sample 1).

The XRD analysis was performed using an X-ray diffractometer D8 ADVANCE produced by Bruker AXS. CuKα rays with a wavelength λ of 0.15418 nm were used as an X-ray source and a scanning range was 2θ=2 to 30 deg.

Figure 10:
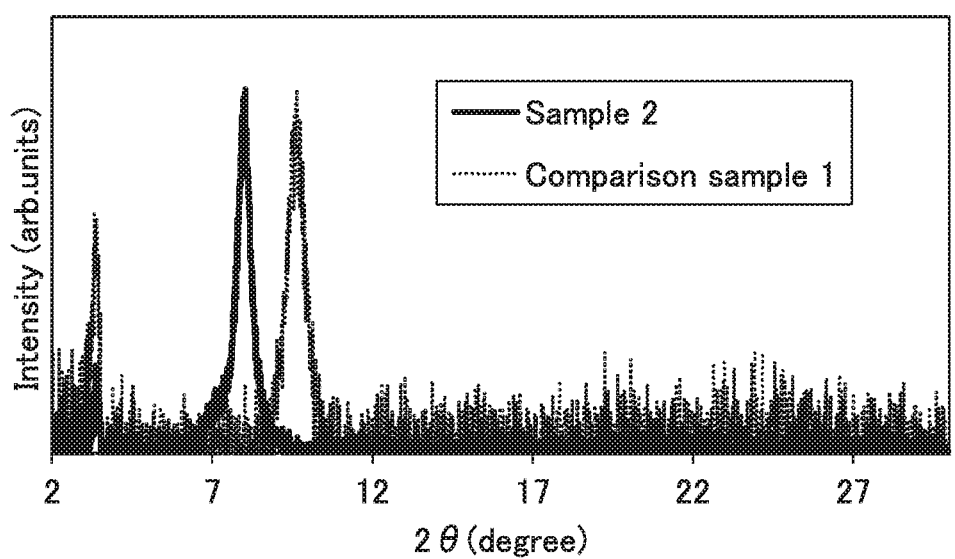
FIG. 10 shows results of XRD measurements.

FIG. 10 shows XRD spectra of Sample 2 and Comparison sample 1. The horizontal axis represents the diffraction angle 2θ [deg.] and the vertical axis represents the X-ray diffraction intensity (arbitrary unit) in each of FIG. 10.

The XRD spectrum of Sample 2 had a peak at a diffraction angle of around 8 degrees. Thus, the average interlayer distance of Sample 2 was calculated to be 1.1 nm.

The XRD spectrum of Comparison sample 1 had a peak at a diffraction angle of around 9.72 degrees. Thus, the average interlayer distance of Comparison sample 1 was calculated to be 0.91 nm.

The average interlayer distance was calculated by the Bragg formula: 2d×sin θ=λ. Here, θ is an incident angle of an X-ray where an X-ray diffraction peak is obtained, d is distance between planes, and λ is a wavelength of an X-ray used for the XRD analysis.

Thus, it was found that the average interlayer distance in Sample 2 increased compared with Comparison sample 1.

Accordingly, it was found that the average interlayer distance in Sample 2 increased owing to chemical modification. In the above-described manner, the chemically modified graphene compounds of one embodiment of the present invention were synthesized.

This application is based on Japanese Patent Application Serial No. 2016-205177 filed with Japan Patent Office on Oct. 19, 2016 and Japanese Patent Application Serial No. 2016-205178 filed with Japan Patent Office on Oct. 19, 2016, the entire contents of which are hereby incorporated by reference.

What is claimed is:

1. A solid electrolyte comprising:
a graphene compound, and
a lithium salt,
wherein:
the graphene compound comprises a structure represented by a general formula (G1)

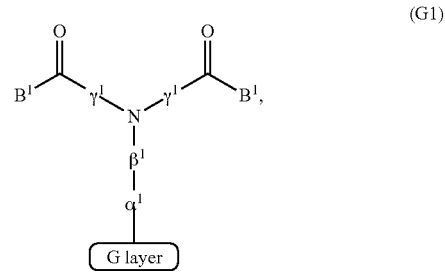

G layer represents a graphene layer,
$\alpha^1$ represents an ether bond, an ester bond, or a bond represented by a general formula (α-1)

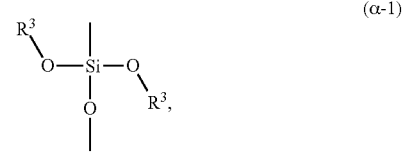

$\beta^1$ and $\gamma^1$ each independently represent a substituted or unsubstituted alkylene group having 1 to 10 carbon atoms, $B^1$ represents an alkoxy group or an alkylamino group, and $R^3$ represents hydrogen or a substituted or unsubstituted alkyl group having 1 to 10 carbon atoms.

2. The solid electrolyte according to claim 1, wherein:

$B^1$ is a group represented by a general formula (B-2)

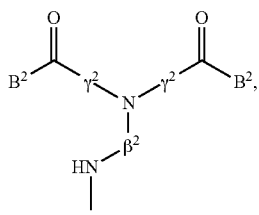

(B-2)

$\beta^2$ and $\gamma^2$ each independently represent a substituted or unsubstituted alkylene group having 1 to 10 carbon atoms, and $B^2$ represents an alkoxy group or an alkylamino group.

3. The solid electrolyte according to claim 2, wherein:

$B^2$ is a group represented by a general formula (B-3)

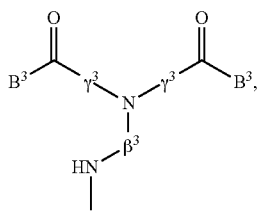

(B-3)

$\beta^3$ and $\gamma^3$ each independently represent a substituted or unsubstituted alkylene group having 1 to 10 carbon atoms, and $B^3$ represents an alkoxy group or an alkylamino group.

4. The solid electrolyte according to claim 3, wherein:

$B^3$ is a group represented by a general formula (B-4)

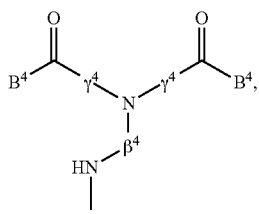

(B-4)

$\beta^4$ and $\gamma^4$ each independently represent a substituted or unsubstituted alkylene group having 1 to 10 carbon atoms, and $B^4$ represents an alkoxy group or an alkylamino group.

5. The solid electrolyte according to claim 4, wherein:

$B^4$ is a group represented by a general formula (B-5)

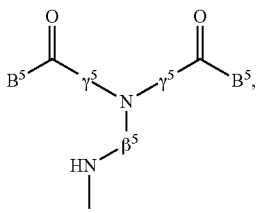

(B-5)

$\beta^5$ and $\gamma^5$ each independently represent a substituted or unsubstituted alkylene group having 1 to 10 carbon atoms, $B^5$ is represented by a general formula (B-1)

(B-1)

and $R^4$ represents a substituted or unsubstituted alkyl group having 1 to 10 carbon atoms.

6. A power storage device comprising:
the solid electrolyte according to claim 1;
an exterior body;
a positive electrode current collector; and
a negative electrode current collector.

7. A manufacturing method of the solid electrolyte according to claim 1, comprising the steps of:
forming a mixture comprising graphene oxide and a compound represented by a general formula (E1)

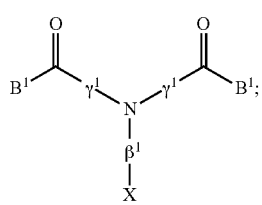

(E1)

and
filtering the mixture to collect a residue,
wherein:
the residue comprises the graphene compound, and
X represents halogen, a trialkoxysilyl group, or a trichlorosilyl group.

8. A manufacturing method of a graphene compound, comprising the steps of:
manufacturing a first graphene compound by the manufacturing method of a graphene compound according to claim 7;
forming a second mixture comprising the first graphene compound and a diamine; and filtering the second mixture to collect a second residue,
wherein the second residue comprises a second graphene compound.

9. A manufacturing method of a graphene compound, comprising the steps of:
   manufacturing a third graphene compound by the manufacturing method of a graphene compound according to claim 7;
   forming a third mixture comprising the third graphene compound and acrylic ester; and
   filtering the third mixture to collect a third residue,
   wherein the third residue comprises a fourth graphene compound.

* * * * *